United States Patent
Fernandes

(10) Patent No.: US 9,669,046 B2
(45) Date of Patent: *Jun. 6, 2017

(54) BIODEFENSES USING TRIAZOLE-CONTAINING MACROLIDES

(71) Applicant: CEMPRA PHARMACEUTICALS, INC., Chapel Hill, NC (US)

(72) Inventor: Prabhavathi Fernandes, Chapel Hill, NC (US)

(73) Assignee: Cempra Pharmaceuticals, Inc., Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/725,247

(22) Filed: May 29, 2015

(65) Prior Publication Data

US 2016/0082028 A1 Mar. 24, 2016

Related U.S. Application Data

(63) Continuation of application No. 13/125,550, filed as application No. PCT/US2009/061978 on Oct. 24, 2009, now Pat. No. 9,072,759.

(60) Provisional application No. 61/162,109, filed on Mar. 20, 2009, provisional application No. 61/108,134, filed on Oct. 24, 2008, provisional application No. 61/108,168, filed on Oct. 24, 2008, provisional application No. 61/108,112, filed on Oct. 24, 2008, provisional application No. 61/108,110, filed on Oct. 24, 2008, provisional application No. 61/108,137, filed on Oct. 24, 2008.

(51) Int. Cl.
| | | |
|---|---|---|
| *A61K 31/70* | (2006.01) | |
| *A01N 43/04* | (2006.01) | |
| *A61K 31/7048* | (2006.01) | |
| *A61K 31/7052* | (2006.01) | |
| *A61K 31/424* | (2006.01) | |
| *A61K 31/7056* | (2006.01) | |
| *C07D 498/04* | (2006.01) | |
| *C07H 17/08* | (2006.01) | |

(52) U.S. Cl.
CPC ........ *A61K 31/7048* (2013.01); *A61K 31/424* (2013.01); *A61K 31/70* (2013.01); *A61K 31/7052* (2013.01); *A61K 31/7056* (2013.01); *C07D 498/04* (2013.01); *C07H 17/08* (2013.01)

(58) Field of Classification Search
None
See application file for complete search history.

(56) References Cited

U.S. PATENT DOCUMENTS

| | | |
|---|---|---|
| 1,354,753 A | 10/1920 | Howard |
| 2,180,006 A | 11/1939 | Hasche |
| 3,668,282 A | 6/1972 | Below |
| 3,843,787 A | 10/1974 | Fabrizio |
| 4,312,866 A | 1/1982 | Caruso |
| 4,331,803 A | 5/1982 | Watanabe |
| 4,474,768 A | 10/1984 | Bright |
| 4,742,049 A | 5/1988 | Baker |
| 4,886,792 A | 12/1989 | Djokic |
| 4,990,602 A | 2/1991 | Morimoto |
| 5,211,955 A | 5/1993 | Legros |
| 5,444,051 A | 8/1995 | Agouridas |
| 5,527,780 A | 6/1996 | Agouridas |
| 5,543,400 A | 8/1996 | Agouridas |
| 5,614,614 A | 3/1997 | Agouridas |
| 5,635,485 A | 6/1997 | Agouridas |
| 5,656,607 A | 8/1997 | Agouridas |
| 5,747,467 A | 5/1998 | Agouridas |
| 5,760,233 A | 6/1998 | Agouridas |
| 5,770,579 A | 6/1998 | Agouridas |
| 5,834,428 A | 11/1998 | Drucker |
| 5,985,844 A | 11/1999 | Heck |
| 6,011,142 A | 1/2000 | Bonnet |
| 6,020,521 A | 2/2000 | Randolph |
| 6,028,181 A | 2/2000 | Or |
| 6,096,714 A | 8/2000 | Agouridas |
| 6,096,922 A | 8/2000 | Lal |
| 6,121,432 A | 9/2000 | Bonnet |
| 6,270,768 B1 | 8/2001 | OConnell |
| 6,313,101 B1 | 11/2001 | Denis |
| 6,395,300 B1 | 5/2002 | Straub et al. |
| 6,395,710 B1 | 5/2002 | Chu |
| 6,407,074 B1 | 6/2002 | Bronk |
| 6,407,257 B1 | 6/2002 | Agouridas et al. |
| 6,420,535 B1 | 7/2002 | Phan |
| 6,437,106 B1 | 8/2002 | Stoner |
| 6,440,941 B1 | 8/2002 | Denis |
| 6,455,505 B2 | 9/2002 | Agouridas |
| 6,515,116 B2 | 2/2003 | Suh |

(Continued)

FOREIGN PATENT DOCUMENTS

| | | |
|---|---|---|
| CN | 1354753 | 6/2002 |
| CN | 101045063 | 10/2007 |

(Continued)

OTHER PUBLICATIONS

Bryskier Clinical Microbiology and Infection (2000), vol. 6, pp. 661-669.*

Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,. beta.-unsaturated ketone." The Journal of Organic Chemistry 53.10 (1988): 2340-2345.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

(Continued)

*Primary Examiner* — Patrick Lewis
(74) *Attorney, Agent, or Firm* — Brannon Sowers & Cracraft PC

(57) ABSTRACT

Use of macrolide and ketolide antibiotics for the treatment of acute exposure and diseases caused by biodefense pathogens is described.

20 Claims, 10 Drawing Sheets

(56) References Cited

U.S. PATENT DOCUMENTS

| | | |
|---|---|---|
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,163,924 B2 | 1/2007 | Burger |
| 7,332,476 B2 | 2/2008 | Burger |
| 7,375,234 B2 | 5/2008 | Sharpless |
| 7,419,961 B2 | 9/2008 | Napoletano |
| 7,601,695 B2 | 10/2009 | Liang et al. |
| 8,012,943 B2 | 9/2011 | Duffield |
| 8,247,394 B2 | 8/2012 | Fernandes |
| 8,791,080 B2 | 7/2014 | Fernandes |
| 8,796,232 B2 | 8/2014 | Fernandes |
| 9,051,346 B2 | 6/2015 | Pereira |
| 9,200,026 B2 | 12/2015 | Liang |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0005325 A1 | 1/2009 | Bas |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2009/0209547 A1 | 8/2009 | Kim |
| 2010/0216731 A1 | 8/2010 | Pereira |
| 2011/0119604 A1 | 5/2011 | Lo |
| 2011/0195920 A1 | 8/2011 | Fernandes |
| 2012/0071429 A1 | 3/2012 | Duffield |
| 2012/0172323 A1 | 7/2012 | Fernandes |
| 2012/0231995 A1 | 9/2012 | Beck |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0102523 A1 | 4/2013 | Bartizal |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| EP | 0248279 A2 | 12/1987 |
| EP | 0680967 A1 | 11/1995 |
| EP | 1024145 A2 | 8/2000 |
| EP | 1167375 | 1/2002 |
| GB | 891817 | 3/1962 |
| JP | S59175414 | 10/1984 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008526948 | 7/2008 |
| JP | 2008534504 | 8/2008 |
| JP | 2009500356 | 1/2009 |
| JP | 2009502788 | 1/2009 |
| JP | 5914335 | 5/2016 |
| RU | 2230748 | 6/2004 |
| WO | 9736912 | 10/1997 |
| WO | 9856800 A1 | 5/1998 |
| WO | 9830574 A1 | 7/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |
| WO | 0062783 A2 | 10/2000 |
| WO | 0110878 A1 | 2/2001 |
| WO | 0250092 A1 | 6/2002 |
| WO | 03004509 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 2007143507 | 12/2007 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011032052 | 3/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |
| WO | 2014152326 | 9/2014 |
| WO | 2014165792 | 10/2014 |
| WO | 2015181723 | 12/2015 |

OTHER PUBLICATIONS

Champney et al., 'Structure-Activity Relationships for Six Ketolide Antibiotics', Current Microbiology, 42:203-10 (2001).

Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Or et al., 'Design, Synthesis, and Antimicrobial Activity of 6-0-Substituted Ketolides Active Against Resistant Respiratory Tract Pathogens', J. Med. Chem., 43:1045-49 (2000).

PCT Search Report and Written Opinion for PCT/US2011/037330 completed Aug. 26, 2011.

(56) References Cited

OTHER PUBLICATIONS

Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Plata, Daniel J., et al."The synthesis of ketolide antibiotic ABT-773 (cethromycin)." Tetrahedron 60.45 (2004): 10171-10180.
Romero et al., 'An efficient entry to new sugar modified ketolide antibiotics' Tetrahedron Letters, vol. 46, 2005, pp. 1483-1487.
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Vince, R., Almquist, R. G., Ritter, C. L., and Daluge, S., Antimicrobial Agents and Chemotherapy, vol. 8, No. 4, 1975, 439-443.
Zhenkun Ma & Peter A. Nemoto "Discovery and Development of Ketolides as a New Generation of MacrolideAntimicrobial Agents" Curr Med Chem-Anti-Infective Agents 1:15-34 (2002).
Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).
Berge, Stephen M., et al., "Pharmaceutical Salts", 1977, Journal of Pharmaceutical Sciences, vol. 66, No. 1, pp. 1-19.
Bermudez, Luiz E., et al., "Telithromycin is Active Against *Mycobacterium avium* in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.
Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.
Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Holzer, G., et al., "Kα1,2 and Kβ1,3 X-Ray Emission Lines of the 3d Transition Metals", Dec. 1997, Physical Review, vol. 56, No. 6, pp: 4554-4568.
Inglesby, Thomas V., et al., "Anthrax as a Biological Weapon, 2002", 2002, Journal of the American Medical Association, vol. 287, No. 17, pp: 2236-2252.
Laine, Loren, et al., "Prospective comparison of H&E, Giemsa and Genta stains for the diagnosis of Helicobacter pylori," 1997, Gastrointestinal Endoscopy, vol. 45, No. 6, pp: 463-467.
Lee, Adrian, et al., "A standard mouse model of Helicobacter pylori infection: introducing the Sydney Strain," 1997, Gastroenterology, vol. 112, pp: 1386-1397.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Patel, Ramesh N., "Stereoselective Biocatalysis", 2000, Bristol-Myers Squibb Research Institute; pp. 775-797.
Barcia-Macay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp: 841-851.

Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp: 799, 800.
Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp: 3973-3979.
Duffy, L., et al., Fluoroquinolone resistance in Ureaplasma parvum in the United States, J Clin Microbiol 44:1590-1591 (2006).
Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).
Lemaire, Sandrine, et al., "Cellular Accumulation and Pharmacodynamic Evaluation of the Intracellular Activity of CEM-101, a Novel Fluoroketolide, Against *Staphylococcus aureus*, Listeria Monocytogenes and Legionella Pneumophila in Human THP-1 Macrophages", 2009, Antimicrobial Agents and Chemotherapy. vol. 53, No.9, pp: 3734-3743.
Li, X., et al., Emerging macrolide resistance in Mycoplasma pneumoniae in children: detection and characterization of resistant isolates, Pediatr Infect Dis J, 28:693-696 (2009).
Physicians' Desk Reference, p. 2905, (2007).
Vennerstrom, Jonathan L., et al., "Identification of an Antimalarial Synthetic Trioxolane Drug Development Candidate", 2004, Letters to Nature, vol. 430, pp. 900-904.
Waites, K.B., et al., Mycoplasmas and ureaplasmas as neonatal pathogens, Clin Microbiol Rev 18:757-89 (2005).
Zuckerman, "Macrolides and ketolides: azithromycin, clarithromycin, telithromycin", Infectious Disease Clinics of North America, vol. 18, (2004), pp. 621-649.
Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.
PCT International Search Report and Written Opinion for PCT/US2011/029424, mailed May 25, 2011.
Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.
Caira MR, "Crystalline polymorphism of orgainic compounds," Design of Organic Solids, Topics in Current Chemistry, Springer Berlin Heidelberg, 1998, p. 163-208.
Pathak et al., "Enzymatic Protecting Group Techniques in Organic Synthesis," Stereosel, Biocatal., 2000; pp. 775-797.
Katz, Leonard, and Gary W. Ashley. "Translation and protein synthesis: macrolides." Chemical reviews 105.2 (2005): 499-528.
Threlfall, Terence L. "Analysis of organic polymorphs. A review." Analyst 120.10 (1995): 2435-2460.
Petit, Samuel, and Gérard Coquerel. "The amorphous state." Polymorphism: In the Pharmaceutical Industry 10 (2006): 1.
Organic Compounds Crystal Manufacture Handbook—Principles and Knowhow, 2008, pp. 57 to 84.
Hancock, Bruno C., Sheri L. Shamblin, and George Zografi. "Molecular mobility of amorphous pharmaceutical solids below their glass transition temperatures." Pharmaceutical research 12.6 (1995): 799-806.
Ashizawa, Kazuhide, "Physico-Chemical Studies on the molecular Details of Drug Crystals," Phar Tech Japan, 2002, vol. 18, No. 10. pp. 81-96.
PCT Search Report and Written Opinion prepared for PCT/US2009/061978 mailed Dec. 9, 2009.
European Search Report for EP 09 82 2827, dated Mar. 21, 2012.
International Search Report for PCT/US2009/061977, dated Dec. 23, 2009, (3 pages).
PCT Search Report/Written Opinion prepared for PCT/US2010/048540, mailed Oct. 21, 2010.

(56) References Cited

OTHER PUBLICATIONS

Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.

Sumerkan, B., Aygen, B., Doganay, M., & Sehmen, E. (1996). Antimicrobial susceptibility of Bacillus anthracis against macrolides. Salisbury Med Bull Supplement, 87, 138.

Maurin, M., Mersali, N. F., & Raoult, D. (2000). Bactericidal activities of antibiotics against intracellular Francisella tularensis. Antimicrobial agents and chemotherapy, 44(12), 3428-3431.

Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus Pseudomycoides and Bacillus thuringiensis to 24 antimicrobials using Sensititre® automated microbroth dilution and Etest® agar gradient diffusion methods. Journal of antimicrobial chemotherapy, 60(3), 555-567.

Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.

Still, J. G., et al. "Single Oral Dose Pharmacokinetics and Safety of CEM-101 in Healthy Subjects." 46th Annual Meeting. Idsa, 2008.

Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.

Chen, M., Muri, E. M., Jacob, T. M., & Williamson, J. S. (2003). Synthesis and bioactivity of erythromycin derivatives. Medicinal chemistry research, 12(3), 111-129.

Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.

Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.

Putnam S. D. et al, Antimicrobial Characterization of Solithromycin (Cem-101), A Novel Fluroroketolide: Activity Against *Staphlococci* and Enterococci. International Journal of Antimicrobial Agents, vol. 37, No. 1, 2011, pp. 39-45.

Written Opinion, Singapore Application No. 11201405895U; Intellectual Property Office of Singapore; Mar. 31, 2015, 6 pages.

Database WPI Week 200822 Thomson Scientific, London, GB; AN 2008-D02982.

Zimmermann, Torsten, et al. "Comparative tolerability of intravenous azithromycin, clarithromycin and erythromycin in healthy volunteers." Clinical Drug Investigation 21.8 (2001): 527-536.

Luke, D. R., and G. Foulds. "Toleration of intravenous azithromycin." The Annals of pharmacotherapy 31.9 (1997): abstract only.

Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.

Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.

Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.

International Search Report for PCT/US2015/015353, dated May 14, 2015, (8 pages).

Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.

Amsden, G. W. "Anti-inflammatory effects of macrolides" an underappreciated benefit in the treatment of community-acquired respiratory tract infections and chronic inflammatory pulmonary conditions?. Journal of Antimicrobial Chemotherapy 55.1 (2005): 10-21.

International Search Report Written Opinion for PCT/US2008/080936 completed Dec. 8, 2008.

de Jong, J. T., et al. "[Large-scale, acute, bacterial gastroenteritis caused by the enterotoxin of *Staphylococcus aureus* after a barbecue]." Nederlands tijdschrift voor geneeskunde 148.43 (2004): 2136-2140.

Raj, Pushker. "Pathogenesis and laboratory diagnosis of *Escherichia coli*—associated enteritis." Clinical microbiology Newsletter 15.12 (1993): 89-93.

Ikeue, T., et al. "[Pneumonia caused by Nocardia nova]." Nihon Kokyuki Gakkai zasshi= the journal of the Japanese Respiratory Society 39.7 (2001): 492-497.

Thakkar, Shyam, and Radheshyam Agrawal. "A case of *Staphylococcus aureus* enterocolitis: a rare entity." Gastroenterology & hepatology 6.2 (2010): 115-117.

Wain, Harry, and Paul A. Blackstone. "Staphylococcal gastroenteritis." The American journal of digestive diseases 1.10 (1956): 424.

Boyce, Thomas G., "Staphylococcal Food Poisoning," Merck Manuals (2015) 2 pages.

Lv Yang et al., "Polymorphic Drugs." Oct. 31, 2009, pp. 110-111.

Le Loir, Yves, Florence Baron, and Michel Gautier. "*Staphylococcus aureus* and food poisoning." Genet Mol Res 2.1 (2003): 63-76.

Brittain HG editor "Polymorphism in pharmaceutical solids", Chapter 1, p. 1-10 (Grant DJW) and Chapter 5, p. 183-226 (1999).

Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.

Cotter, Paul D., and Colin Hill. "Surviving the acid test: responses of gram-positive bacteria to low pH." Microbiology and Molecular Biology Reviews 67.3 (2003): 429-453.

Wain, Harry, and Paul A. Blackstone. "Staphylococcal Gastroenteritis." The American journal of digestive diseases 1.10 (1956): 424-429.

Lyczak, J. B., Cannon, C. L., & Pier, G. B. (2002). Lung infections associated with cystic fibrosis. Clinical microbiology reviews, 15(2), 194-222.

Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.

Bryskier, A. "Ketolides—telithromycin, an example of a new class of antibacterial agents." Clinical Microbiology and Infection 6.12 (2000): 661-669.

Morimoto, Shigeo, et al. "Chemical modification of erythromycins. I. Synthesis and antibacterial activity of 6-O-methylerythromycins A." The Journal of antibiotics 37.2 (1984): 187-189.

Hallgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.

Fernandes, P., et al. Intravenous Formulation of Solithromycin, a Painless Macrolide Antibiotic in a Rabbit Intravenous Injection Model, 2011, 5 pages.

Allen Loyd V Jr, Acidifying Agents, Featured Excipient. International Journal of Pharmaceutical Compounding, Dec. 31, 1999, vol. 3, No. 4, pp. 309 (abstract only).

Yatin R. G. et al., Excipients for Protein Drugs. Excipient Development for Pharmaceutical, Biotechnology, and Drug Delivery Systems, Jul. 28, 2006, pp. 299-300.

Fernandes, P., et al. "Solithromycin Macrolide Antibiotic." Drugs of the Future 36.10 (2011): 751-758.

(56) References Cited

OTHER PUBLICATIONS

Raoul, Jennifer M., Marc R. Peterson, and Theresa C. Peterson. "A novel drug interaction between the quinolone antibiotic ciprofloxacin and a chiral metabolite of pentoxifylline." Biochemical pharmcology 74.4 (2007): 639-646.

Salzer, W. (2005). Antimicrobial-resistant gram-positive bacteria in PD peritonitis and the newer antibiotics used to treat them. Peritoneal Dialysis International, 25(4), 313-319.

\* cited by examiner

FIG. 2

*Bacillus anthracis*

*Yersinia pestis*

*Francisella tularensis*

FIG. 2 (CONTINUED)

Burkholderia mallei

Burkholderia pseudomallei

BIODEFENSES USING TRIAZOLE-CONTAINING MACROLIDES

CROSS-REFERENCE TO RELATED APPLICATIONS

This application claims priority under 35 USC §119(e) to U.S. Provisional Application Ser. No. 61/108,110, filed on Oct. 24, 2008, U.S. Provisional Application Ser. No. 61/108,112, filed on Oct. 24, 2008, U.S. Provisional Application Ser. No. 61/108,134, filed on Oct. 24, 2008, U.S. Provisional Application Ser. No. 61/108,137, filed on Oct. 24, 2008, U.S. Provisional Application Ser. No. 61/108,168, filed on Oct. 24, 2008, and U.S. Provisional Application Ser. No. 61/162,109, filed on Mar. 20, 2009, the entire disclosure of each of which are incorporated herein by reference.

TECHNICAL FIELD

The invention described herein relates to the treatment of acute exposure and diseases caused by biodefense pathogens. In particular, the invention described herein relates to the treatment of acute exposure and diseases caused by biodefense pathogens with macrolide and ketolide antibiotics.

BACKGROUND AND SUMMARY OF THE INVENTION

There continues to be a feared scenario of battlefield use of or domestic terrorist attacks with aerosolized microorganisms leading to mass infections. Given the added possibility of resistance to current treatments through genetic engineering or natural emergence, identifying new effective antibiotics is critical to counter such an attack. An effective therapeutic agent against a spectrum of inhaled pathogens is needed in the armamentarium of therapeutics to combat bioterror and biowarfare. It has been surprisingly discovered that triazole-containing macrolides and ketolides exhibit high activity on various organisms that pose a potential biowarfare and/or bioterror threat.

In one embodiment, compounds, compositions, methods, and medicaments are described herein for treating diseases arising from one or more bioterror and/or biowarfare agents. Illustrative agents include *Bacillus anthracis* (BA), *Yersinia pestis* (YP), *Francisella tularensis* (FT), *Burkholderia mallei* (BM), and *B. pseudomallei* (BP). In another embodiment, compounds, compositions, methods, and medicaments are described herein for treating diseases arising from one or more bioterror and/or biowarfare agents selected from *B. anthracis, Y. pestis, F. tularensis*, and *B. mallei*. It has been surprising discovered herein that the triazole-containing compounds described herein are highly active on *F. tularensis*. In another embodiment, the compounds, compositions, methods, and medicaments are useful as post-exposure prophylaxis agents, such as medical countermeasures, following an exposure or inhalation of a one or more bioterror and/or biowarfare agents. In another embodiment, the compounds, compositions, methods, and medicaments are useful in treating diseases caused by an exposure or inhalation of a one or more bioterror and/or biowarfare agents, including, but not limited to, pneumonia, plague, tularemia, meliodosis, and the like.

In one illustrative embodiment, compounds of Formula (I) are described herein (I)

including pharmaceutically acceptable salts, hydrates, solvates, esters, and prodrugs thereof.

In one aspect, $R_{10}$ is hydrogen or acyl. In another aspect, X is H; and Y is $OR_7$; where $R_7$ is a monosaccharide or disaccharide, alkyl, aryl, heteroaryl, acyl, or $C(O)NR_8R_9$, where $R_8$ and $R_9$ are each independently selected from the group consisting of hydrogen, hydroxy, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl.

In another aspect, V is $C(O)$, $C(=NR_{11})$, $CH(NR_{12}, R_{13})$, or $N(R_{14})CH_2$, where $N(R_{14})$ is attached to the C-10 carbon of the compounds of Formulae 1 and 2; wherein $R_{11}$ is hydroxy or alkoxy, $R_{12}$ and $R_{13}$ are each independently selected from the group consisting of hydrogen, hydroxy, akyl, aralkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl.

In another aspect, W is H, F, Cl, Br, I, or OH.

In another aspect, A is $CH_2$, $C(O)$, $C(O)O$, $C(O)NH$, $S(O)_2$, $S(O)_2NH$, $C(O)NHS(O)_2$. In another aspect, B is $(CH_2)_n$ where n is an integer ranging from 0-10, or B is an unsaturated carbon chain of 2-10 carbons. In another aspect, C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureido, or carbamoyl.

In another embodiment, compositions including a therapeutically effective amount of one or more compounds of formula (I), or the various subgenera thereof are described herein. The pharmaceutical compositions may include additional pharmaceutically acceptable carriers, diluents, and/or excipients.

BRIEF DESCRIPTION OF THE DRAWINGS

FIG. 2. CEM-101 Minimum Inhibitory Concentration Distributions are shown in bar graph form FIG. 3. Comparative susceptibilities of *S. aureus* ATCC 25923 and *L. monocytogenes* EGD to CEM-101, TEL, AZI, and CLR, based on MIC determinations in pH-adjusted broth.

Both drugs were used at an extracellular concentration of either 0.7 (top panels) or 4 (bottom panels) mg/liter. MICs of CEM-101 and AZI were 0.06 and 0.5 mg/liter, respectively. All values are means±standard deviations (SD) of three independent experiments (when not visible, SD bars are smaller than the symbols).

Figure 5:
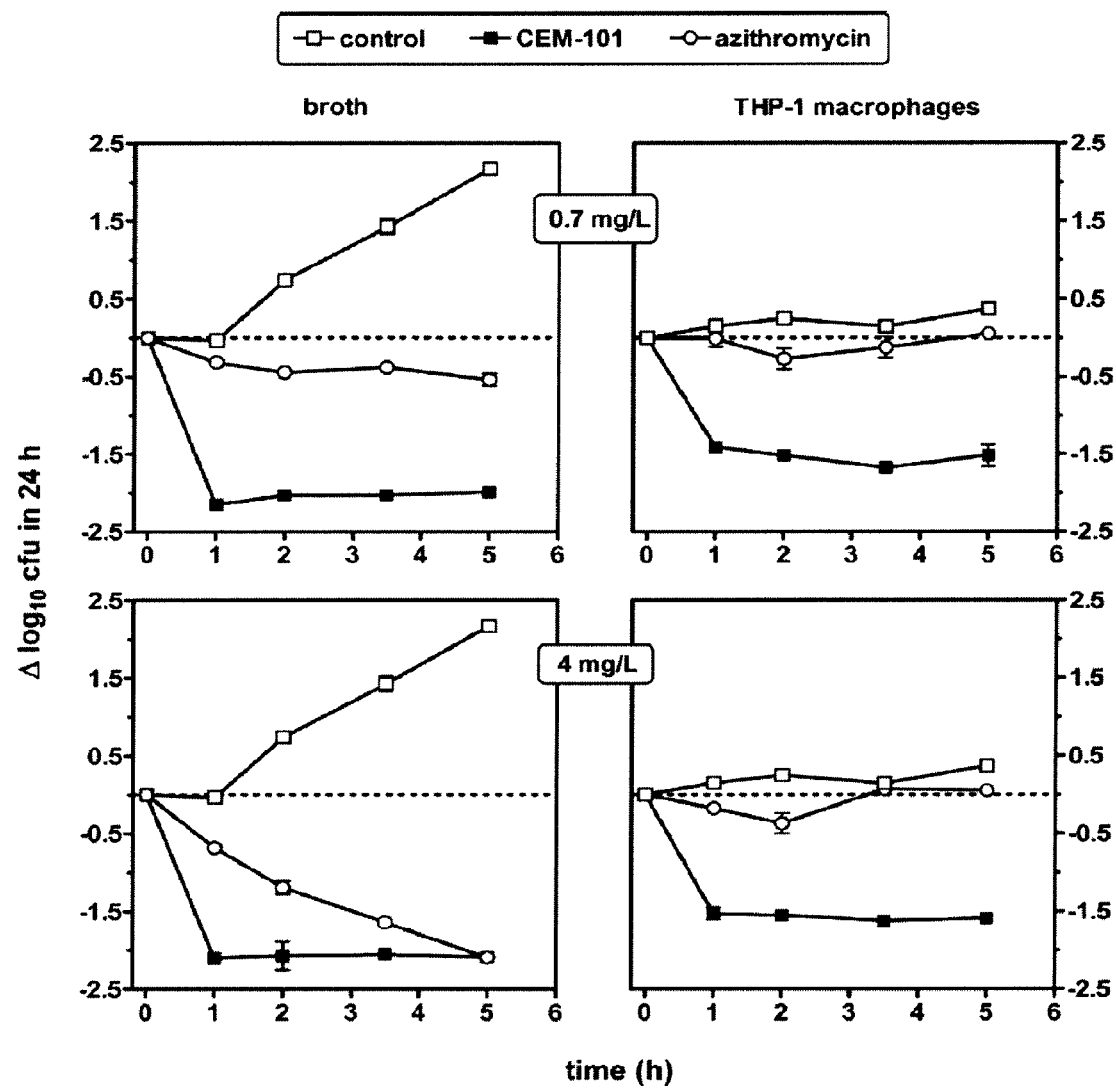

FIG. 5. Concentration-effect relationships for CEM-101, TEL, CLR, and AZI toward *S. aureus* (ATCC 25923) in broth (left panels) and after phagocytosis by THP-1 macrophages (right panels). The ordinate shows the change in CFU (Δ log CFU) per ml (broth) or per mg of cell protein (THP-1 macrophages) at 24 h compared to the initial inoculum. The abscissa shows the concentrations of the antibiotics as follows: (i) top panels, weight concentrations (in mg/liter) in broth (left) or in the culture medium (right) and (ii) bottom panels, multiples of the MIC as determined in broth at pH 7.4. All values are means±standard deviations (SD) of three independent experiments (when not visible, SD bars are smaller than the symbols). Statistical analysis based on global analysis of curve-fitting parameters (one-way analysis of variance); the only significant difference is between CEM-101 and AZI in broth (P=0.04). Numerical values of the pertinent pharmacological descriptors and statistical analysis of their differences are shown in Table 1.

Figure 6:
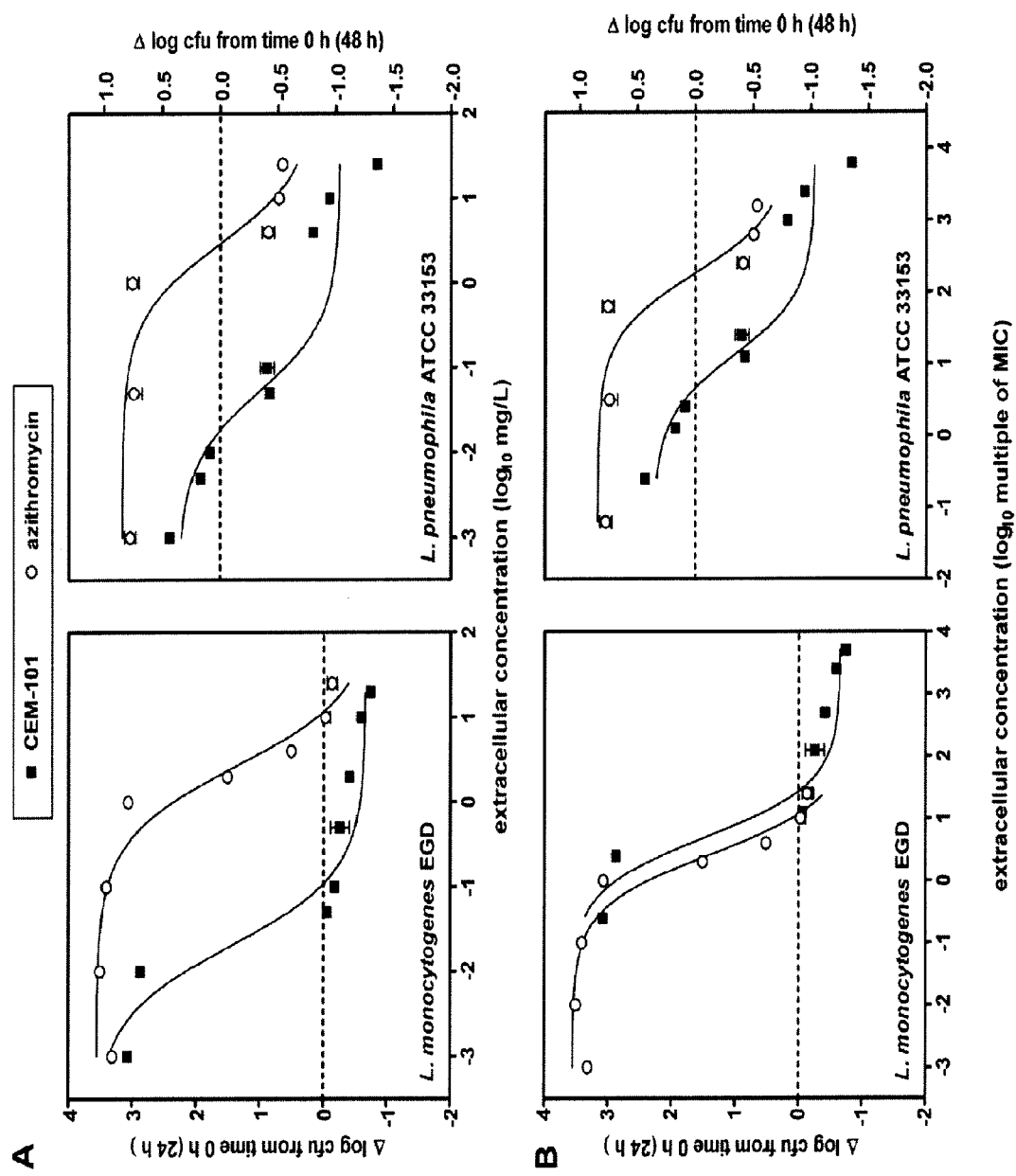

FIG. 6. Concentration-effect relationships for CEM-101 and AZI toward intraphagocytic *L. monocytogenes* (strain EGD, left panels) and *L. pneumophila* (strain ATCC 33153, right panels). The ordinate shows the change in CFU (Δ log CFU) per mg of cell protein at 24 h (*L. monocytogenes*) or 48 h (*L. pneumophila*) compared to the initial postphagocytosis inoculum. The abscissa shows the concentrations of the antibiotics as follows: (i) top panels, weight concentrations (in mg/liter); (ii) bottom panels, multiples of the MIC as determined in broth at pH 7.4. All values are means±standard deviations (SD) of three independent experiments (when not visible, SD bars are smaller than the symbols).

Figure 7:
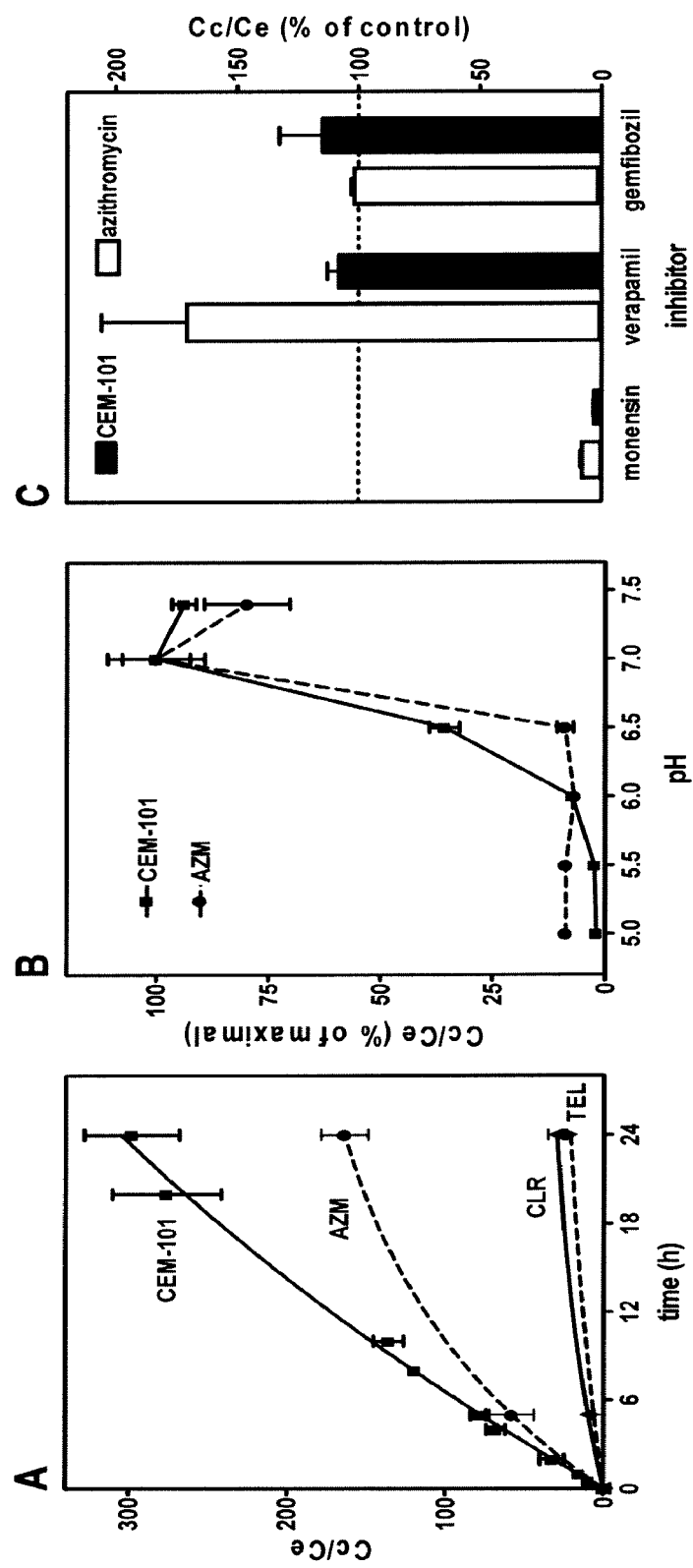

FIG. 7. Accumulation of CEM-101 versus comparators in THP-1 cells at 37° C. (all drugs at an extracellular concentration of 10 mg/liter). (A) Kinetics of accumulation (AZI); Cc, intracellular concentration; Ce, extracellular concentration); (B) influence of the pH of the culture medium on the accumulation (30 min) of CEM-101 (solid symbols and solid line) and AZI (open symbols and dotted line); (C) influence of monensin (50 µM; 2-h incubation), verapamil (150 µM; 24-h incubation), or gemfibrozil (250 µM; 24-h incubation) on the cellular accumulation of AZI and CEM-101. All values are means±standard deviations (SD) of three independent determinations (when not visible, SD bars are smaller than the symbols).

Figure 8:
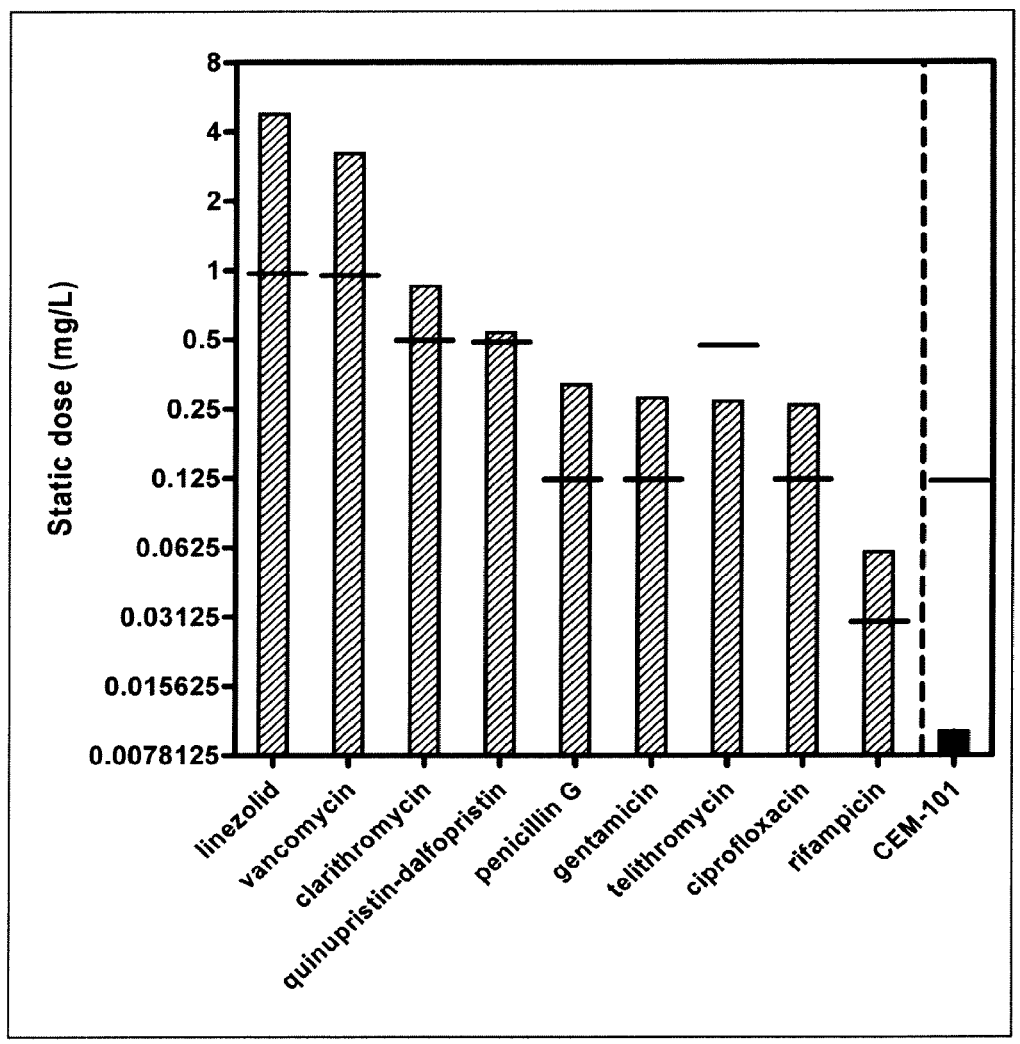

FIG. 8. Intracellular activity: comparative studies with other anti-staphylococcal agents. Comparative dose-static response of antibiotics against intracellular *Staphylococcus aureus* (strain ATCC 25923) in THP-1 macrophages. Bars represent the MICs (in mg/L) or the extracellular static dose.

Figure 9:
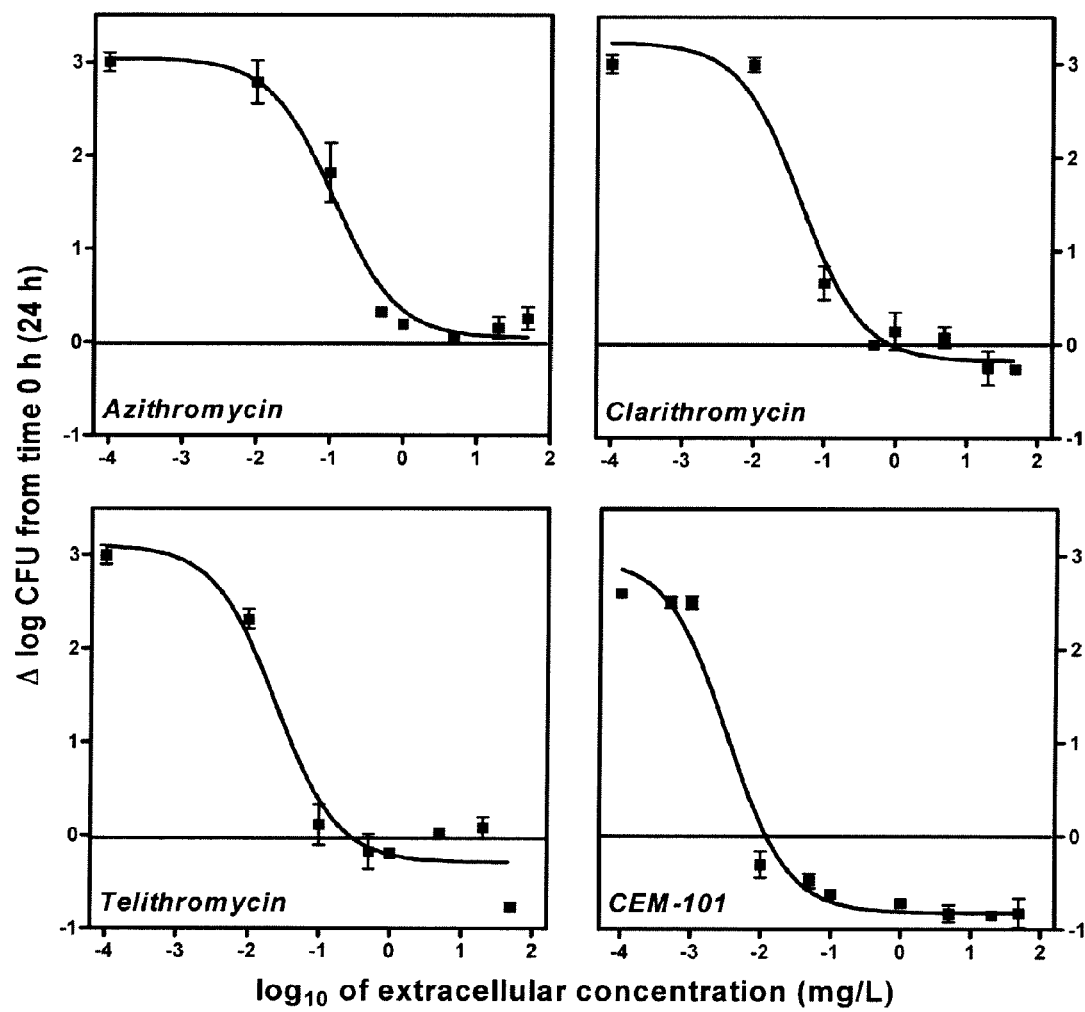

FIG. 9. Intracellular Activity of CEM-101 compared to AZI, CLR, and TEL, expressed as a dose response curve of Δ log CFU from time 0 to 24 hours versus log dose.

DETAILED DESCRIPTION

In one embodiment, compounds are described herein that are active intracellularly. It has also been discovered herein that the intracellular accumulation and intracellular activity of triazole-containing macrolides was not affected by Pgp or Multidrug Resistant Protein (MRP) inhibitors. Accordingly, it is believed that the compounds described herein are not substrates or are poor substrates of P-glycoprotein (plasma or permeability gycoprotein, Pgp). It is appreciated that Pgp is an efflux mechanism that may lead to resistance by some organisms against certain antibiotics, such as has been reported for AZI and ERY in macrophages in which both antibiotics are substrates of the P-glycoprotein. Accordingly, it has been surprisingly found that the compounds described herein accumulate intracellulary. In addition to the intracellular accumulation, it has been surprisingly discovered that the triazole-containing macrolide and ketolide compounds described herein have high intracellular activity. It has also been surprising found herein that the compounds described herein have lower protein binding than is typical for macrolides at lower pH, such as the pH found in bacterial infections, including but not limited to abscesses. It is appreciated that the lack of intracellular activity typically observed with anti-bacterial agents, including other macrolides and ketolides, may be due to high protein binding, and/or to the relatively lower pH of the intracellular compartments, such as is present in abscesses.

However, even when not removed by active efflux, the concentration of other anti-bacterial agents, including other macrolides and ketolides, in macrophages may not be efficacious in treating disease because of the low pH of the lysozomal compartment. For example, the acidic environment prevailing in the phagolysosomes (where one or more of *B. anthracis, Y. pestis, F. tularensis*, and/or *B. mallei* may sojourn during its intracellular stage) may impair the activity of antibiotics, such as the AZI, CLR and TEL. It has been unexpectedly found that the compounds described herein retain their anti-bacterial activity at low pH. It is appreciated that the intracellular activity of the compounds described herein may be an important determinant for fast and complete eradication and, probably also, for prevention of resistance in the target organism.

Lack of effective antimicrobial therapy results in intracellular survival of bacteria, which remains a major cause of bacterial spreading, life-threatening therapeutic failures, and establishment of chronic, relapsing infections. These situations are observed during the course of infections caused by many biodefense organisms, including *B. anthracis, Y. pestis, F. tularensis*, and *B. mallei*.

While it has been reported that intracellular accumulation of an antibiotic is indicative of efficient activity against bacteria, pharmacodynamic evaluation of a large series of commonly used antibiotics has revealed that other parameters such as intracellular bioavailability and modulation of activity in the infected compartment are also important. The observations described herein confirm and extend previous observations made with macrolides in this context due to the surprising differential behavior exhibited by the triazole-containing macrolides described herein, compared to known macrolide and ketolides, such as TEL, AZI, and CLR.

It is surprisingly found that triazole-containing macrolides accumulate to a considerably larger extent than the comparators, including AZI, and consistently expresses greater potency (decreased values of $E_{50}$ and $C_s$) while showing similar maximal efficacy ($E_{max}$) to comparators. Without being bound by theory, it is believed that this indicates that the improvements resulting from the structural modifications introduced in CEM-101 relate to modulation of pharmacokinetic properties and intrinsic activity (including its reduced susceptibility to physico-chemical conditions prevailing in the infected compartment) rather than to a change in its mode of action. Thus, triazole-containing macrolides exhibit the essentially bacteriostatic character of macrolides, but express it better in the intracellular milieu and at considerably lower extracellular concentrations than the comparators.

Without being bound by theory, it is believed that the cellular accumulation of triazole-containing macrolides, such as CEM-101, results from the general mechanism of proton trapping of weak organic bases envisaged for all macrolides as accumulation is almost completely suppressed, in parallel with AZI, by exposure to acid pH or to the proton ionophore monensin. Based on the general model of diffusion/segregation of weak bases in acidic membrane-bound compartments, accumulation is determined by the number of ionizable groups and the ratios between the membrane permeability coefficients of the unionized and ionized forms of the drug. While CEM-101 has two ionizable functions, the pKa of the aminophenyltriazole is calculated to be less than 4, suggesting that the molecule is largely monocationic (similar to CLR and TEL) at neutral and even at lysosomal pH (~5). In contrast, AZI has two ionizable functions with $pK_as>6$ and is therefore dicationic intracellularly. CEM-101, however, possesses a fluoro substituent in position 2, which should make it more lipophilic than CLR or TEL. Without being bound by theory, it is believed that the ratio of the permeability constants of the unionized and ionized forms of CEM-101 in comparison with LR or TEL may be as important as the number of ionizable functions to determine the level of cellular accumulation of weak organic bases. Without being bound by theory, it is believed that the greater cellular accumulation of CEM-101 may be partially due to its lack of susceptibility to Pgp-mediated efflux (which is expressed by THP-1 macrophages under our culture conditions) in contrast to azithromycin and other macrolide or ketolide antibiotics.

It has been observed that many known macrolides have a large volume of distribution, which it is believed is related to their ability to accumulate inside eukaryotic cells by diffusion/segregation in acidic compartments, namely lysosomes and related vacuoles. As a consequence, known macrolides had been considered candidates for the treatment of infections localized in these compartments. Thus, it might be assumed that macrolides are suitable for treating infections caused by typical intracellular pathogens such as *B. anthracis, Y. pestis, F. tularensis*, and *B. mallei*. However, direct quantitative comparisons between intracellular and extracellular activities using facultative intracellular pathogens, such as *S. aureus* or *L. monocytogenes*, suggest that known macrolides express only a minimal fraction of their antibacterial potential intracellularly, especially considering their great intracellular accumulation. This minimized antibacterial potential against organisms replicating in phagolysosomes and related vacuoles is believed to be related to acidic pH which is known to reduce the activity of known macrolides. Another factor is that some organisms, such as *B. anthracis, Y. pestis, F. tularensis*, and *B. mallei*, may actually replicate in other subcellular compartments. In addition, certain macrolides, such as AZI, are subject to active efflux from macrophages, which further contributes to suboptimal intracellular activity.

In contrast, the cellular accumulation and intracellular activity of the triazole-containing compounds described herein, using models that have been developed for the study of the intracellular pharmacodynamics of antibiotics, is substantially improved over known macrolides, including ketolides. Thus, the compounds described herein maintain the maximal efficacy of their MICs, and show greater potency against intracellular forms of for example, *B. anthracis, Y. pestis, F. tularensis*, and *B. mallei* compared to TEL, AZI, and CLR. Without being bound by theory, it is believed that this improved intracellular potency of the triazole-containing compounds described herein results from the combination of the higher intrinsic activity against *B. anthracis, Y. pestis, F. tularensis*, and *B. mallei* coupled with the retained activity at low pH, and the ability to distribute to a wide variety of intracellular compartments.

In another embodiment, the triazole-containing macrolide and ketolide compounds have intracellular activity, such as intracellular activity against *B. anthracis, Y. pestis, F. tularensis*, and *B. mallei*. Survival of these organism within eukaryotic cells is critical for the persistence of infection. It is appreciated that routine susceptibility testing are usually determined against extracellular bacteria only, and therefore may be misleading in their prediction of efficacy against intracellular organisms.

In another embodiment, the compounds, methods, and medicaments described herein include a therapeutically effective amount of one or more compounds described herein, wherein the therapeutically effective amount is an amount effective to exhibit intracellular antibacterial activity.

In another embodiment, compounds are described herein that are bactericidal. In another embodiment, the compounds, methods, and medicaments described herein include a therapeutically effective amount of one or more compounds described herein, wherein the therapeutically effective amount is an amount effective to exhibit bactericidal activity, including in vivo bactericidal activity. It has been reported that macrolides are generally bacteriostatic. Bacteriostatic compounds do not kill the bacteria, but instead for example inhibit growth and reproduction of bacteria without killing them; killing is accomplished by bactericidal agents. It is understood that bacteriostatic agents must work with the immune system to remove the microorganisms from the body. Bacteriostatic antibiotics may limit the growth of bacteria via a number of mechanisms, such as by interfering with bacterial protein production, DNA replication, or other aspects of bacterial cellular metabolism. In contrast, bactericidal antibiotics kill bacteria; bacteriostatic antibiotics only slow their growth or reproduction. Several bactericidal mechanism have been reported, including disrupting cell wall precursor leading to lysis, binding irreversibly to 30s ribosomal subunit, reducing translation fidelity leading to inaccurate protein synthesis, and inhibit protein synthesis due to premature separation of the complex between mRNA and ribosomal proteins. The final result is bacterial cell death.

In another embodiment, the compounds, compositions, methods, and medicaments described herein include a therapeutically effective amount of one or more compounds described herein, wherein the therapeutically effective amount is an amount effective to exhibit bactericidal activity against one or more of *B. anthracis, Y. pestis, F. tularensis*, and *B. mallei*. Without being bound by theory, it is believed herein that treating such diseases using bacteriostatic agents may be unsuccessful in two respects. First, simply stopping the progression of the disease with a bacteriostatic agent may be insufficient because the immune system may not intervene to assist in curing the disease at a necessary level. For example, some bacterial organisms are not killed by the immune system because they reside in intracellular compartments. Thus, once the treatment course has ended, rapid recurrence of disease may result. Second, because some portion of the bacterial population will likely be eliminated, the remaining population may be selected for resistance development. It is believed herein that an intracellularly active agent, and/or an intracellularly active and bactericidal agent, will be efficacious in treating such diseases. In one illustrative embodiment, compounds described herein that achieve an intracellular concentration of 20× the MIC of the targeted bacteria. It has been reported that most, if not all, macrolide antibiotics, though bactericidal in vitro, are only bacteriostatic in vivo. For example, as described herein, when the time between the last dose of compound was extended, the bioload reduction levels remained the same for the triazole-containing compounds described herein, indicating a bactericidal response. In contrast, the TEL and CLR dose groups demonstrated bioload increases when the time interval was extended. Thus, those latter two macrolide/ketolide agents demonstrated a more classical bacteriostatic response.

CEM-101 was also found to have potent in vitro activity against *B. anthracis* which compares favorably with that of antibiotics currently approved (ciprofloxacin, MIC$_{90}$ 0.031 ug/ml) or proposed (cethromycin, MIC$_{90}$ 0.063 ug/ml) for post-exposure anthrax indications.

Figure 1:
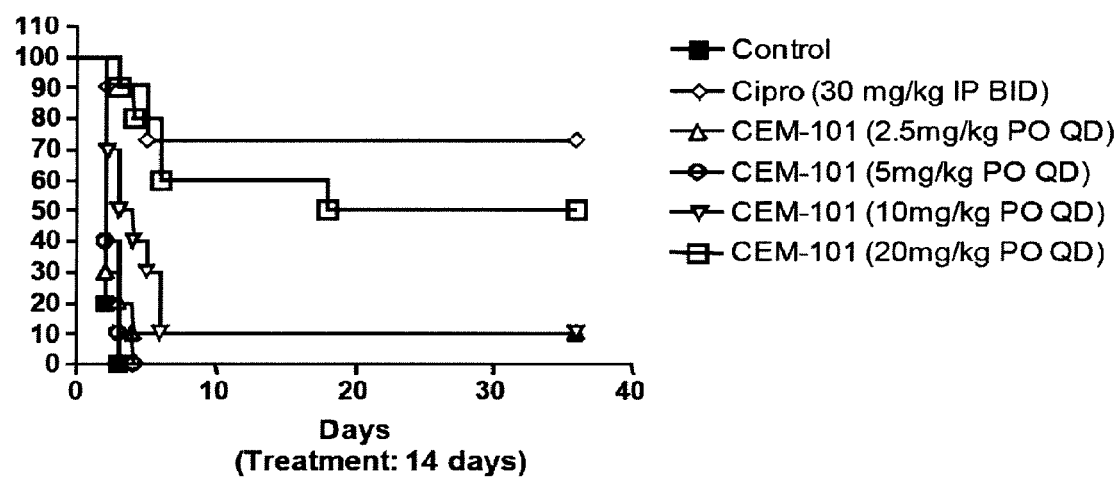
FIG. 1. Preliminary in vivo studies in animal models of disease also demonstrate protection against these pathogens.

As shown in FIG. 1, dose-dependent activity (percent survival) against aerosolized *B. anthracis* is observed over 14 days of oral dosing. Of particular significance is the fact that the protective doses shown here (e.g. 2.5-20.00 mg/kg) also provide high serum and tissue levels of CEM-101 in rodent models, levels which are achievable with safe dosing regimens in human trials. Based on accrued GLP toxicology data, it should be possible to administer CEM-101 for longer intervals (e.g. 30-60 days) as recommended for management of post exposure inhalational anthrax. (Drusano, et al., Antimicrobial Agents and Chemotheraspy, November, 2008, p 3973-3979, Vol 52, No 11.) These prolonged prophylactic regimens are required to eradicate vegetative cells following germination of dormant spores, known to exist for a variable and potentially extended duration in pulmonary tissues of exposed subjects prior to development of clinical symptoms (Inglesby, et al., JAMA 2002; 287(17) 2236-2252). Moreover, given the uncertainties about duration of spore latency after exposure or even after discontinuation of a 30-60 day prophylactic regimen, acute therapy with an oral formulation may be required in selected symptomatic subjects in this biodefense scenario.

In cellular models, CEM-101 is significantly more active than other antibacterial agents against organisms located intracellularly. It is active against resistant bacteria, including multi-drug resistant bacteria. Evidence of bacterial resistance to CEM-101 in vitro is observed. Without being bound by theory, it is believed that those examples that become resistant are likely not to have a survival advantage as they would have multiple mutations that decrease viability and virulence The capacity of CEM-101 to accumulate in tissues and to achieve high intracellular concentrations, with antimicrobial potency, is a pharmacologic characteristic, because intracellular parasitism underlies the pathophysiology of disease due to the biothreat agents of concern here. FIG. 6 shows that macrophage uptake and intracellular killing of *Legionella pneumophila* (lysosomal compartment) and *Listeria monocytogenes* (cytoplasm) by CEM-101 is even more active than by other macrolide agents tested (Lemaire, et al., Antimicrob. Agents. Chemother. 53: 3734-3743, 2009). Intracellular concentrations that are 20-200 fold higher than achieved in plasma is facilitated by rapid uptake into the cell and evasion of the efflux pump P-glycoprotein, thus allowing effective eradication of replicating intracellular pathogens. CEM-101, unlike azithromycin and cethromycin, is not a substrate for P-glycoprotein.

Several in vivo protocols wherein CEM-101 was repeatedly dosed in toxicology studies in rodents and non human primates have demonstrated tissue levels of CEM-101~17-100× higher than peak plasma levels. CEM-101 accumulated in tissues and concentrations were highest in liver, spleen, lung, and salivary gland. This relationship was confirmed in rodent ADME studies using radiolabeled CEM-101. When administered orally at 100 mg/kg, lung tissue to plasma radioactivity ratios of ~13:1 were observed in male and female animals. After IV dosing at 20 mg/kg, the data was more variable and lung/plasma ratios of 17.6 for males and 6.2 for females were observed. Cmax and AUC ranged from 0.022 µg/mL and 0.04 µg·h/mL to 1.96 µg/mL and 28.60 µg·h/mL across the dose range. The mean CEM-101 $t_{max}$ increased from 1.5 to 6.0 hours and the mean terminal half-life increased from 2.2 to 7.9 hours over the 50 to 1600 mg dose range.

In another illustrative embodiment, compounds of Formula (I) are described herein where X and Y are taken together with the attached carbon to form a C(O) group. In another embodiment, X is H, Y is OR$^7$, where R$^7$ is a monosaccharide radical, such as cladinosyl. In another embodiment, compounds of Formula (I) are described herein where W is fluoro. In another embodiment, compounds of Formula (I) are described herein where A and B are taken together to form an alkylene group, including but not limited to propylene, butylene, and pentylene. In another embodiment, compounds of Formula (I) are described herein where A and B are taken together to form butylene. In another embodiment, compounds of Formula (I) are described herein where A and B are taken together to form pentylene. In another embodiment, compounds of Formula (I) are described herein where A and B are taken together to form butylenes and C is 2-pyridinyl or aminophenyl, such as 3-aminophenyl. In another embodiment, compounds of Formula (I) are described herein where A and B are taken together to form propylenes, butylenes, or pentylenes; and C is aminophenyl, such as 3-aminophenyl. In another embodiment, compounds of Formula (I) are described herein where A and B are taken together to form pentylene and C is 3-pyridinyl or benzotriazole. In another embodiment, compounds of Formula (I) are described herein where C is an optionally substituted aryl or heteroaryl group. In another embodiment, compounds of Formula (I) are described herein where V is a carbonyl group. In another embodiment, compounds of Formula (I) are described herein where R$^{10}$ is hydrogen. In another embodiment, X is H, Y is OR$^7$, where R$^7$ is a monosaccharide radical, such as cladinosyl, and C is 3-pyridinyl or benzotriazolyl.

In another embodiment, C is optionally substituted phenyl, such as phenyl, halophenyl, haloalkylphenyl, aminophenyl, and the like, optionally substituted pyridinyl, such as 2-pyridinyl and 3-pyridinyl, optionally substituted benzotriazole, and the like.

In another embodiment, A and B are taken together to form butylene or pentylene, and X and Y are taken together with the attached carbon to form a C(O) group.

In another embodiment, compounds described in any of the preceding embodiments wherein V is C(O) are described. In another embodiment, compounds described in any of the preceding embodiments wherein W is H or F are described. In another embodiment, compounds described in any of the preceding embodiments wherein A is CH$_2$, B is (CH$_2$)$_n$, and n is an integer from 2-4 are described. In another embodiment, compounds described in any of the preceding embodiments wherein C is aryl or heteroaryl are described. In another embodiment, compounds described in any of the preceding embodiments wherein C is 3-aminophenyl or 3-pyridinyl are described. In another embodiment, compounds described in any of the preceding embodiments wherein $R_{10}$ is hydrogen. In another embodiment, compounds described in any of the preceding embodiments wherein A and B are taken together to form butylene or pentylene, and X and Y are taken together with the attached carbon to form a C(O) group. In another embodiment, compounds described in any of the preceding embodiments wherein A and B are taken together to form butylene or pentylene, and X and Y are taken together with the attached carbon to form a C(O) group, and W is F.

In another embodiment, an antibacterial composition is described herein, wherein the composition includes an effective amount of one or more compounds described herein, and a pharmaceutically acceptable carrier, excipient, or diluent therefor, or a combination thereof.

As used herein, the term "composition" generally refers to any product comprising the specified ingredients in the specified amounts, as well as any product which results, directly or indirectly, from combinations of the specified ingredients in the specified amounts. Illustratively, compositions may include one or more carriers, diluents, and/or excipients. The compounds described herein may be formulated in a therapeutically effective amount in conventional dosage forms for the methods described herein, including one or more carriers, diluents, and/or excipients therefor. Such formulation compositions may be administered by a wide variety of conventional routes for the methods described herein in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

In one embodiment, the compounds described herein are administered to a human orally at a dose of about 1 to about 10 mg/kg, about 2 to about 8 mg/kg, or about 4 to about 6 mg/kg of patient body weight. In another embodiment, the daily adult human dose is about 100 to about 1,000 mg, which may be administered qd, bid, tid, and the like. In another embodiment, the daily adult human dose is about 400 to about 600 mg, which may be administered qd, bid, tid, and the like. Such doses may be administered, once, twice, or thrice per day. Illustrative oral unit dosages are 50, 100, 200, and 400 mg (single or divided). Without being bound by theory, it is believed that such illustrative dosages are sufficient to achieve plasma levels of about 1 μg/mL, which may be sufficient to observe bactericidal activity of the compounds described herein, such as for one or more of *B. anthracis, Y. pestis, F. tularensis*, and *B. mallei*. It is appreciated that as described herein, the compounds described herein, including CEM-101, reach high concentration in tissues, such as lung tissues. Without being bound by theory, it is believed herein that the compounds described herein, including CEM-101, may achieve tissue levels that are at least about 10-times the MIC for strains, including macrolide-resistant strains, such as but not limited to *B. anthracis, Y. pestis, F. tularensis*, and *B. mallei*, including resistant strains thereof.

The compounds described herein may be prepared as described herein, or according to US Patent Application Publication No. 2006/0100164 and in PCT International Publication No. WO 2009/055557, the disclosures of which are incorporated herein by reference in their entirety.

Briefly, the synthesis of triazole containing ketolides begins with the known two step preparation of the 12-acyl-imidazole intermediate 4 (Scheme I) from clarithromycin (2). Intermediate 4 is converted into the 11,12-cyclic carbamates 5a-c by the reaction with the corresponding 3-, 4- or 5-carbon linked amino alcohols. Treatment of 5a-c with tosyl chloride provides tosylates 6a-c. Displacement of the tosyl group with $NaN_3$ gives the corresponding azido compounds 7a-c. Cleavage of the cladinose sugar of 7a-c to 8a-8c is accomplished by treatment with HCl in MeOH. Swern oxidation of the 3-hydroxy group of 8a-c gives the corresponding protected ketolides 9a-c which are subsequently deprotected with methanol to afford the required azido ketolides 10a-c, respectively. These azido compounds were reacted with terminally-substituted alkynes in the presence of copper iodide in toluene at 60° C. to regioselectively afford the corresponding 4-substituted-[1,2,3]-triazoles 11a-18a, 11b-18b, and 11c-18c.

The azide of intermediates 10a-c is converted to the 4-substituted-[1,2,3]-triazoles via a cycloaddition reaction with substituted acetylenes. Triazole rings may be formed via a Huisgen 1+3 cycloaddition reaction between an azide and an alkyne resulting in a mixture of 1,4- and 1,5-regioisomers as depicted in Route A of Scheme II. Alternatively. the procedure of Rostovtsev et al.[8] may be followed using the addition of a CuI catalyst to the reaction to selectively or exclusively produce the 1,4-regioisomer as depicted in Route B of Scheme II.

The triazole ring side chain is also incorporated into the clarithromycin ring system. In one embodiment, a butyl alkyl side chain is chosen. It is appreciated that many butyl side chain analogs in the ketolide series have improved antibacterial activity based on in vitro MIC results. Intermediate 7b is directly converted into the 4-substituted-[1,2,3]-triazole via copper catalyzed cyclization with terminally substituted acetlyenes, as shown in Scheme III. The acetate protecting groups of 19a-e are removed with LiOH in methanol to afford the corresponding 4-substituted-[1,2,3]-triazoles 20a-e.

Substitution of the 2-position hydrogen with a fluorine is accomplished by electrophilic fluorination of 9b (Scheme IV) using Selectfluor®. The azido group of intermediate 22 is converted to a series of 4-substituted-[1,2,3]-triazoles 23a-b via the standard conditions.
Scheme I
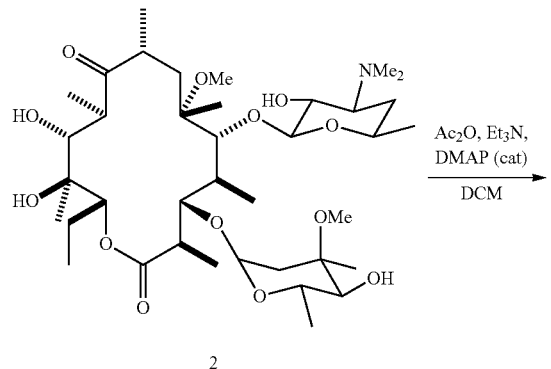
2
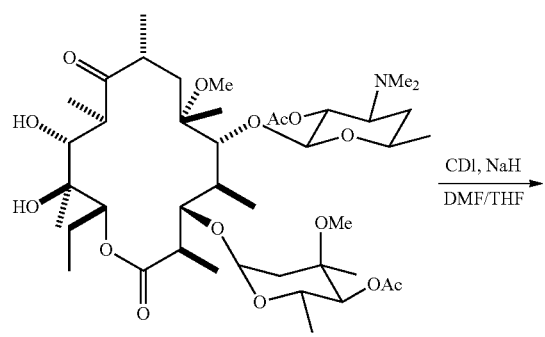
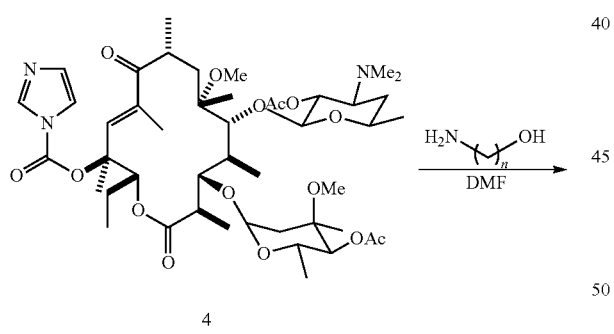
4
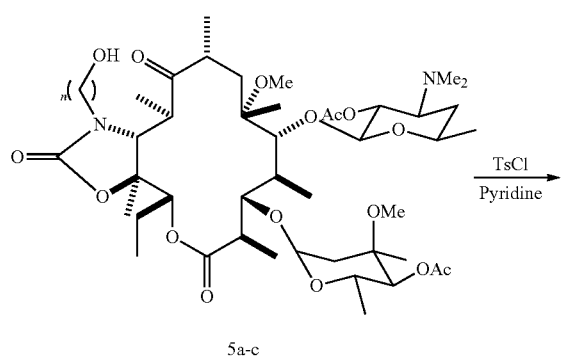
5a-c
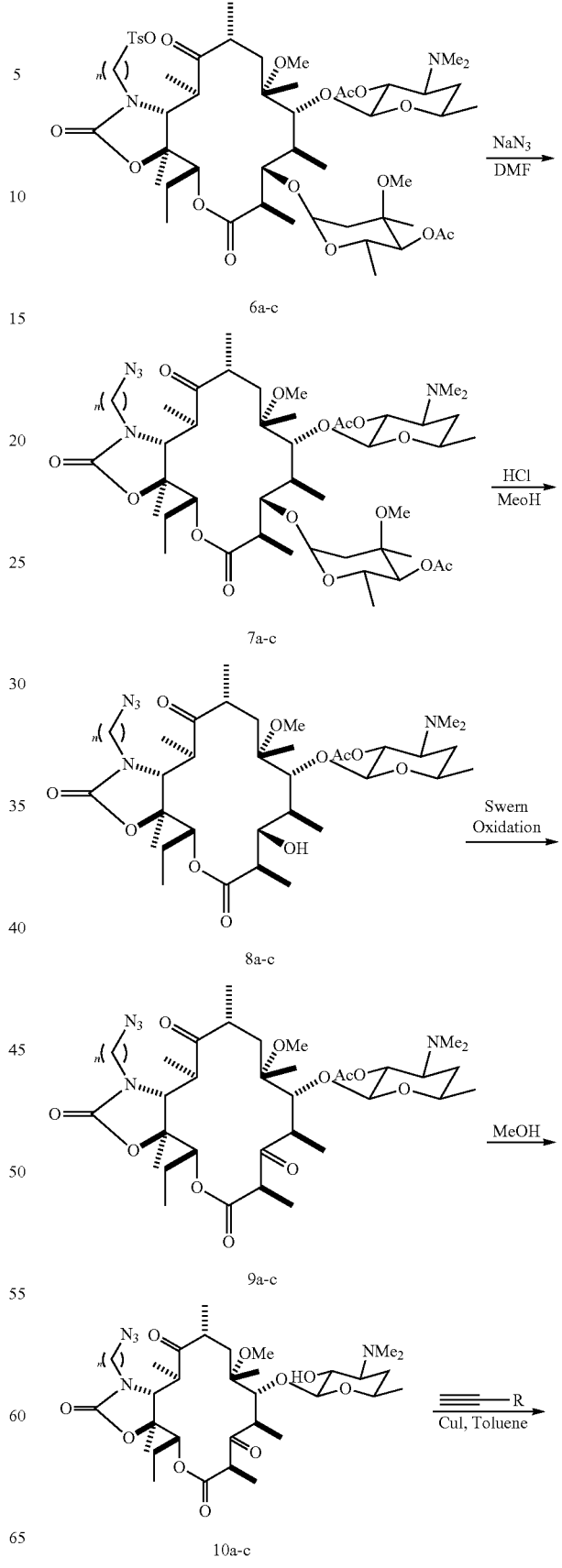
6a-c
7a-c
8a-c
9a-c
10a-c 13
-continued
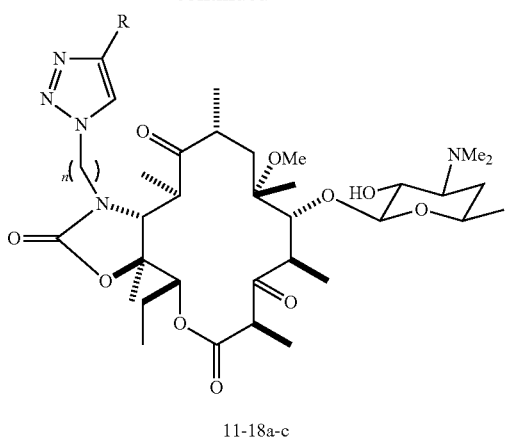
11-18a-c
Scheme II
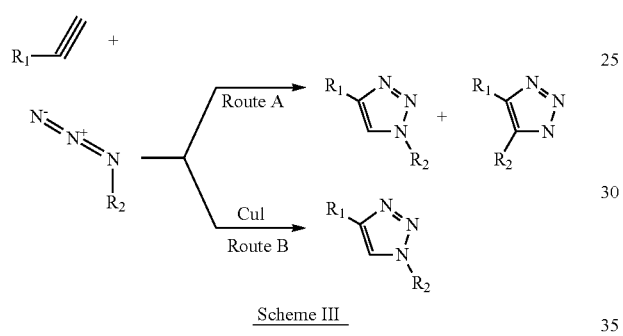
Scheme III
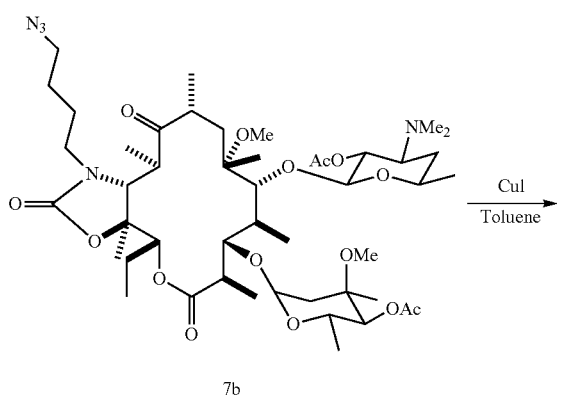
7b
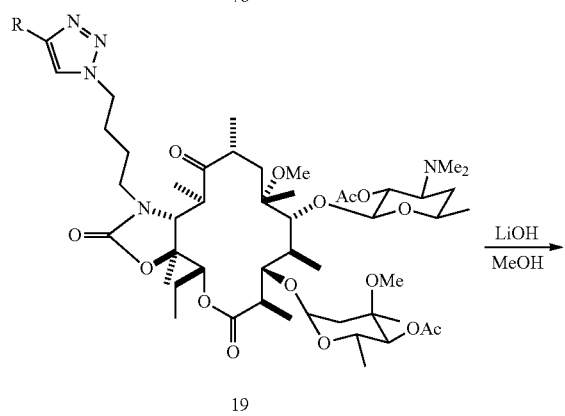
19
14
-continued
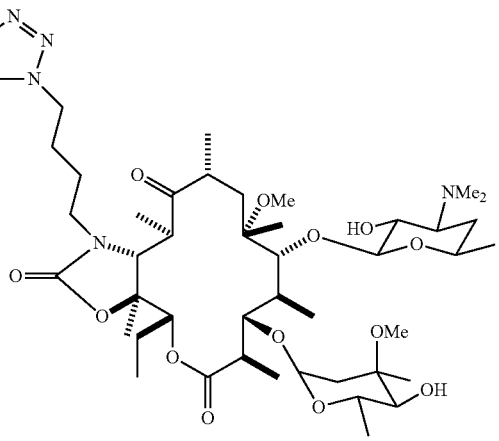
20a-e
Scheme IV
9a
21

-continued

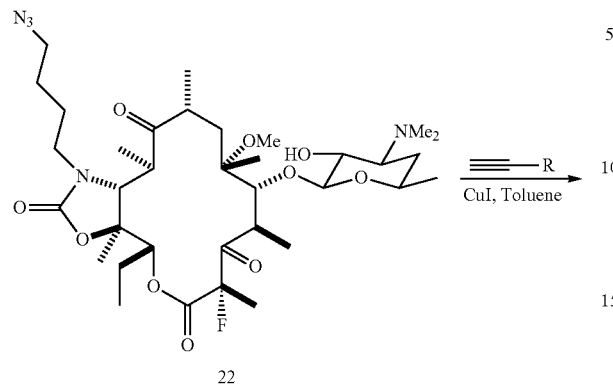

22

≡—R
CuI, Toluene

-continued

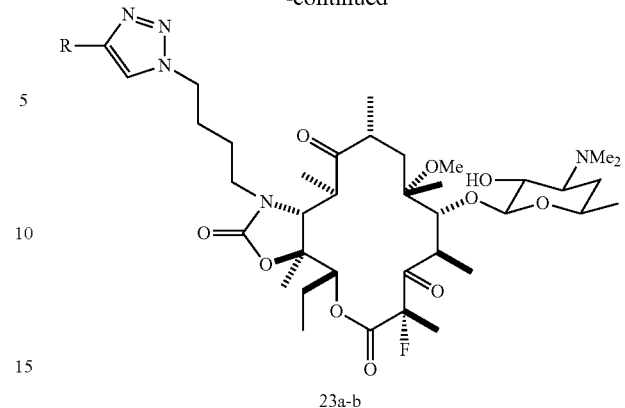

23a-b

In another embodiment, the following compounds are described:

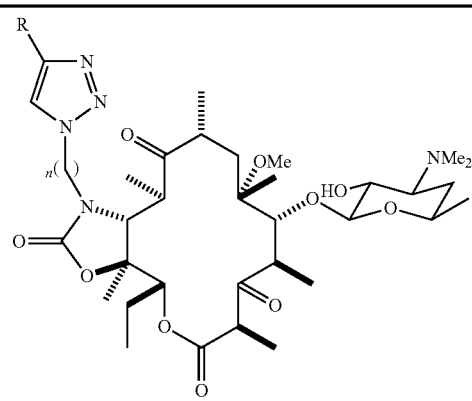

| | | | Minimum inhibitory concentration (μg/mL)[a] | | | | | |
|---|---|---|---|---|---|---|---|---|
| | | | S. aureus | | S. pneumoniae | | | H. influenzae |
| | | | 29213 | 96:11480 Ery-R | 49619 | 163 | 303 | 49247 |
| Entry | R | n | Ery-S | (MLSb) | Ery-S | Ery-R (MefA) | Ery-R (ermB) | Ery-S |
| TEL | | | ≤0.125 | ≤0.125 | ≤0.125 | ≤0.125 | ≤0.125 | 4 |
| AZI | | | ≤0.125 | >64 | ≤0.125 | >64 | >64 | 2 |
| 11a | phenyl | 3 | 1 | 1 | ≤0.125 | ≤0.125 | >64 | >64 |
| 11b | phenyl | 4 | ≤0.125 | 0.25 | ≤0.125 | ≤0.125 | 2 | 8 |
| 11c | phenyl | 5 | ≤0.125 | ≤0.125 | ≤0.125 | ≤0.125 | 0.25 | 16 |
| 12a | 4-Br-phenyl | 3 | 0.25 | 0.5 | ≤0.125 | ≤0.125 | 8 | 64 |
| 12b | 4-Br-phenyl | 4 | ≤0.125 | ≤0.125 | ≤0.125 | ≤0.125 | 8 | 8 |
| 12c | 4-Br-phenyl | 5 | ≤0.125 | ≤0.125 | ≤0.125 | ≤0.125 | 1 | 16 |
| 13a | 4-CF$_3$-phenyl | 3 | 1 | 2 | ≤0.125 | ≤0.125 | 16 | >64 |
| 13b | 4-CF$_3$-phenyl | 4 | 0.25 | 0.25 | ≤0.125 | ≤0.125 | 8 | 8 |
| 13c | 4-CF$_3$-phenyl | 5 | 0.5 | 1 | ≤0.125 | 0.5 | 2 | 64 |

-continued

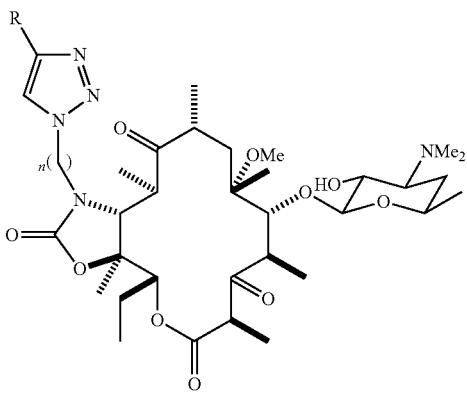

Minimum inhibitory concentration (μg/mL)[a]

| | | | S. aureus | | S. pneumoniae | | | H. influenzae |
|---|---|---|---|---|---|---|---|---|
| | | | | 96:11480 | | | | |
| Entry | R | n | 29213 Ery-S | Ery-R (MLSb) | 49619 Ery-S | 163 Ery-R (MefA) | 303 Ery-R (ermB) | 49247 Ery-S |
| 14a | 2-pyridyl | 3 | 2 | 2 | ≤0.125 | 0.5 | >64 | >64 |
| 14b | | 4 | ≤0.125 | ≤0.125 | ≤0.125 | ≤0.125 | ≤0.125 | 4 |
| 14c | | 5 | ≤0.125 | ≤0.125 | ≤0.125 | ≤0.125 | 0.25 | 64 |
| 15a | 3-pyridyl | 3 | 2 | 2 | ≤0.125 | 1 | >64 | >64 |
| 15b | | 4 | ≤0.125 | 4 | ≤0.125 | 2 | 64 | 64 |
| 15c | | 5 | ≤0.125 | 0.25 | ≤0.125 | 0.25 | 4 | 16 |
| 16a | 3-aminophenyl | 3 | 0.5 | nt | ≤0.125 | ≤0.125 | >64 | 16 |
| 16b | | 4 | ≤0.125 | ≤0.125 | ≤0.125 | ≤0.125 | ≤0.125 | 2 |
| 16c | | 5 | ≤0.125 | ≤0.125 | ≤0.125 | ≤0.125 | 0.25 | 8 |
| 17a | 2,6-dichlorophenoxyethyl | 3 | 1 | 1 | ≤0.125 | ≤0.125 | >64 | >64 |
| 17b | | 4 | ≤0.125 | ≤0.125 | ≤0.12 | ≤0.12 | 1 | 16 |
| 17c | | 5 | 0.25 | 0.5 | ≤0.125 | ≤0.125 | 2 | 32 |
| 18a | benzotriazolyl | 3 | 1 | 2 | ≤0.125 | 0.5 | >64 | >64 |
| 18b | | 4 | 1 | 2 | ≤0.125 | 4 | 64 | 32 |
| 18c | | 5 | ≤0.125 | ≤0.125 | ≤0.125 | ≤0.125 | 64 | 8 |

[a]National Committee for Clinical Laboratory Standards. Methods for Dilution Antimicrobial Susceptibility Tests for Bacteria that Grow Aerobically, 6th ed.; Approved standard: NCCLS Document M7-A6, 2003.

In another embodiment, the following compounds are described:
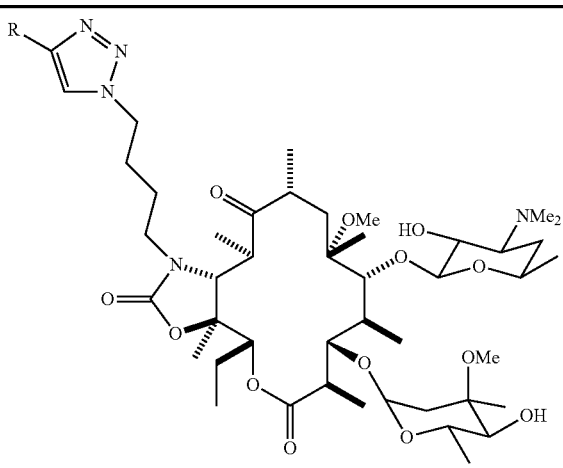
| Entry | R | S. aureus 25923 Ery-S | RN220 | S. pneumoniae 49619 Ery-S | 163 Ery-R (MefA) | 303 Ery-R (ermB) | H. influenzae 49247 Ery-S |
|---|---|---|---|---|---|---|---|
| TEL | | ≤0.25 | 2 | ≤0.125 | ≤0.125 | ≤0.125 | 4 |
| 20a | 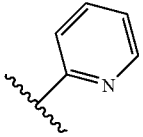 [SMILES: *c1ccccn1] | 0.25 | 8 | ≤0.0625 | 0.125 | 2 | NT |
| 20b | 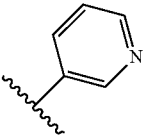 [SMILES: *c1cccnc1] | 0.25 | 8 | ≤0.0625 | ≤0.06 | 1 | NT |
| 20c | 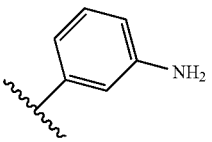 [SMILES: *c1cccc(N)c1] | 1 | 8 | ≤0.0625 | 0.5 | 2 | NT |
| 20d | 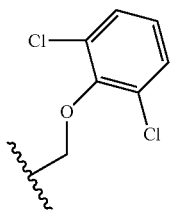 [SMILES: *COc1c(Cl)cccc1Cl] | 1 | 8 | ≤0.0625 | 0.5 | 2 | NT |
| 20e | 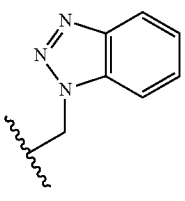 [SMILES: *Cn1nnc2ccccc21] | ≤0.25 | 8 | ≤0.0625 | 0.5 | 2 | NT |

In another embodiment, the following compounds are described:

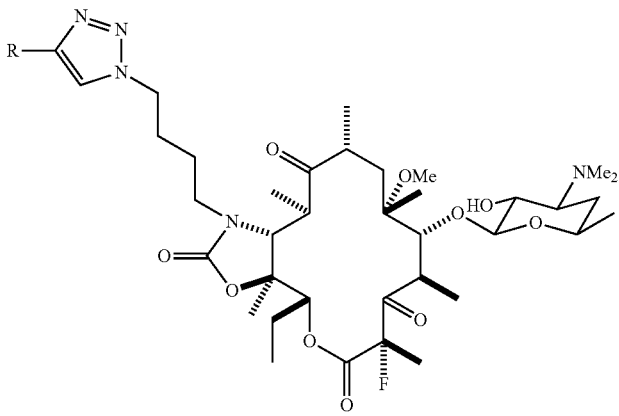

| Entry | R | S. aureus 29213 Ery-S | S. aureus 96:11480 Ery R (MLSb) | S. pneumoniae 49619 Ery-S | S. pneumoniae 163 Ery-R (MefA) | S. pneumoniae 303 Ery-R (ermB) | H. influenzae 49247 Ery-S |
|---|---|---|---|---|---|---|---|
| TEL |   | ≤0.125 | ≤0.125 | ≤0.125 | ≤0.125 | ≤0.125 | 4 |
| AZI |   | ND | ≤0.125 | >64 | ≤0.125 | >64 | >64 |
| 23a | 2-pyridyl | ≤0.125 | ≤0.125 | ≤0.125 | ≤0.125 | ≤0.125 | 2 |
| 23b (CEM-101) | 3-aminophenyl | ≤0.06 | ≤0.125 | ≤0.125 | ≤0.125 | ≤0.125 | 2 |

In each of the foregoing embodiments, the primary screening panel consisted of relevant *Staph. aureus*, *S. pyogenes*, *S. pneumoniae* (including strains resistant to azithromycin and telithromycin). MICs against all pathogens were determined using broth microdilution method as per NCCLS guidelines. Compounds described herein, such as CEM-101 were found to be highly potent having MICs against *S. pneumoniae* (3773) of ≤0.125 μg/mL and *S. pyogenes* (1850) of 0.5 μg/mL, compared to 1 and 8 μg/mL, respectively for Telithromycin. CEM-103 (20c), an analogue of CEM-101 that contains the 3-O-cladinose was found to be less active. Non-heteroaromatic substituted triazole containing ketolides were less active.

The ketolides were tested against erythromycin-sensitive (Ery-S) and erythromycin-resistant (Ery-R) strains of *S. aureus* (29213 (Ery-S) and 96:11480 (Ery-R)), *S. pneumoniae* (49619 (Ery-S) and 163 and 303 (Ery-R)) and *H. influenzae* (49247 (Ery-S)) (Tables 1-3). The broth microdilution method was used to determine the Minimum Inhibitory Concentrations (MICs) against all pathogens as per the Clinical and Laboratory Standards Institute (CLSI).

The chain length of the alkyl side chain had a affected activity (Table 1). For example, the 3-carbon linked phenyl substituted triazole 11a was less active against Ery-S and Ery-R *S. aureus* and was inactive against Ery-R *S. pneumoniae* 303 (ermB) a the tested concentrations, whereas the corresponding 4- and the 5-carbon linked phenyl substituted triazoles 11b and 11c were more active against these organisms. A similar trend was observed for the 2-pyridyl substituted triazoles 14a-c, the 3-amino-phenyl substituted triazoles 16a-c, and the 2,5-dichlorophenoxy substituted triazoles 17a-c.

The 4-carbon linked 2-pyridyl substituted triazole 14b and the 3-amino-phenyl substituted triazole 16b possessed the highest potency against *S. pneumoniae* 303, both having MIC values (≤0.125 μg/mL) comparable to telithromycin. The ketolide containing the 4-carbon linked 3-pyridyl substituted triazole 15b was less active against this strain (MIC of 64 μg/mL). Within this series antibacterial activity was improved by extending the carbon linker to 5 atoms, for example the MIC against *S. pneumoniae* 303 for compound 15c improved from 64 to 4 μg/mL. A similar effect was also observed for the benzo-triazole containing ketolide 18c against *S. aureus* but 18c was still inactive against *S. pneumoniae* 303. It is appreciated that a balance between the length of the linker and nature of the aromatic substitution of the triazole may affect the overall activity against macrolide resistant *S. pneumonia* and *S. aureus*.

A correlation between linker length and activity was also observed for *H. influenzae* (49247) where the most potent ketolide series had the substituted triazole linked through either a 4-carbon (11b-14b, 16b, 17b) or a 5-carbon (15c, 18c) chain. Interestingly, the most potent aromatic series against *H. influenzae* was the 3-amino-phenyl with a 3-, 4- or 5-carbon linker (16a, 16b, 16c) having MICs of 16, 2, and 8 μg/mL, respectively, The macrolides containing a cladinose at the 3 position were all highly active against Ery-S *S. pneumoniae* (49619) (Table 2). However, these analogs were less potent than telithromycin against Ery-R strains. The MICs were significantly higher for the cladinose containing analogs with either 2-pyridyl, 2-aminophenyl or 2,6-dichlorophenyl triazole substituents than for the corresponding ketolides (20a, 20c, and 20d versus 14b, 16b, and 17b). Conversely, antibacterial activity was re-established for ketolide analogs 15b (3-pyridyl) and 18b (benzo-triazole) by replacing the keto with the cladinose group in analogs 20b (3-pyridyl) and 20e (benzo-triazole). The MICs improved from 64 μg/mL for 15b and 18b to 1 and 2 μg/mL for 20b and 20e, respectively. A similar activity trend was also observed for Ery-R *S. pneumoniae* 163 (MefA).

A mixture of 11-N-(4-Azido-butyl)-6-O-methyl-5-(3-dimethylamine-4-deoxy-6-O-acetyl-glu-copyranosyl)-2-fluoro-3-oxo-erythronolide A, 11,12-carbamate (15 mg, 0.019 mmol), 6-Ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform: methanol plus 1% ammonium hydroxide) to give 14 mg of the desired compound. MS: $C_{44}H_{66}FN_7O_{12}$ calculated $M^+=903.5$. Found: $M+H^+=904.5$.

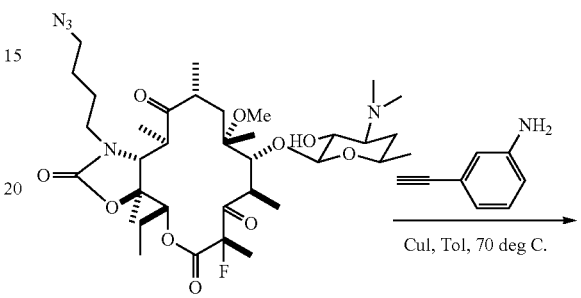

COMPOUND EXAMPLES

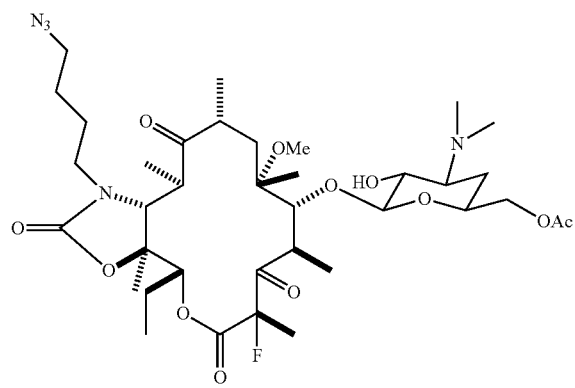 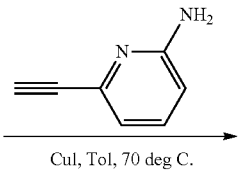

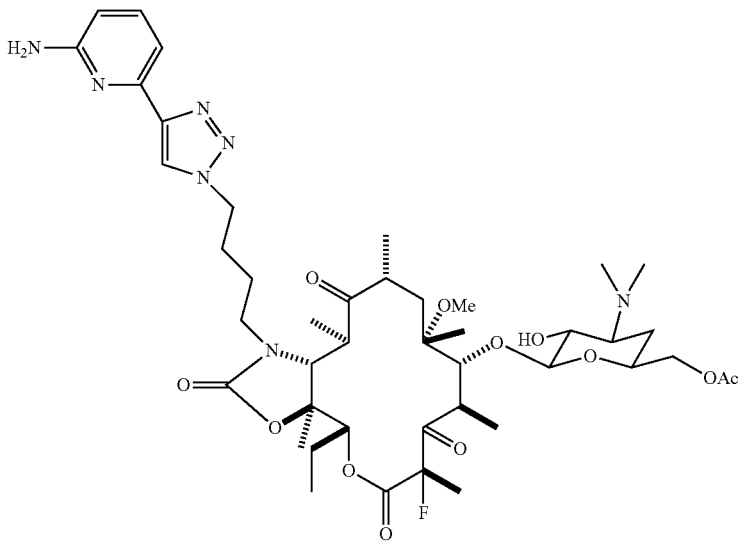

-continued

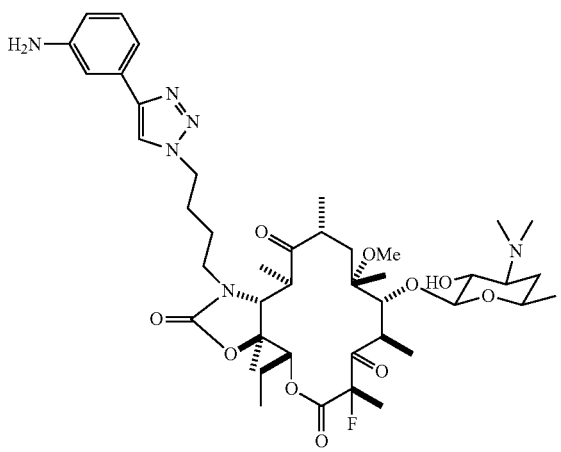

11-N-4-(3-aminophenyl)-[1,2,3]triazol-1-yl]-butyl}-5-desosaminyl-3-oxo-2-fluoro-erythronolide A,-11,12-cyclic carbamate (CEM-101). A mixture of 11-N-(4-azido-butyl)-6-O-methyl-5-desosamynyl-3-oxo-2-fluoro-erythronolide A, 11,12-carbamate (17 mg, 0.023 mmol), 3-Ethynyl-phenylamine (5.4 mg, 0.046 mmol), CuI (1 mg, 0.005 mmol), and toluene (0.2 mL) was heated to 70° C. After 16 h, the mixture was concentrated and directly subjected to silica gel chromatography (9:1, chloroform: methanol plus 1% ammonium hydroxide) to give 17 mg of the desired compound, MS $C_{43}H_{65}FN_6O_{10}$ calculated $M^+=844.47$. Found: $M+H^+=845.5$.

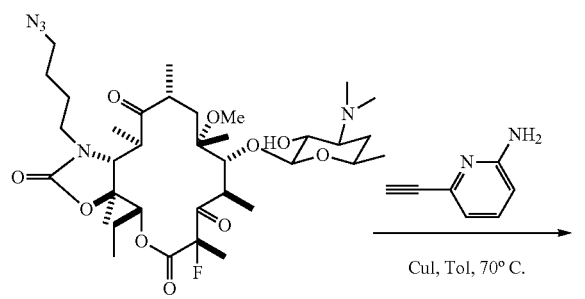

11-N-{4-[4-(6-Amino-pyridin-2-yl)-[1,2,3]triazol-1-yl]-butyl}-5-desosaminyl-3-oxo-2-fluoro-erythronolide A,-11,12-cyclic carbamate. A mixture of 11-N-(4-azido-butyl)-6-O-methyl-5-desosamynyl-3-oxo-2-fluoro-erythronolide A, 11,12-carbamate (15 mg, 0.02 mmol), 6-ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 14 mg of the desired compound OP1357. MS: $C_{42}H_{64}FN_7O_{10}$ calculated $M^+=845.5$. Found: $M+H^+=846.5$.

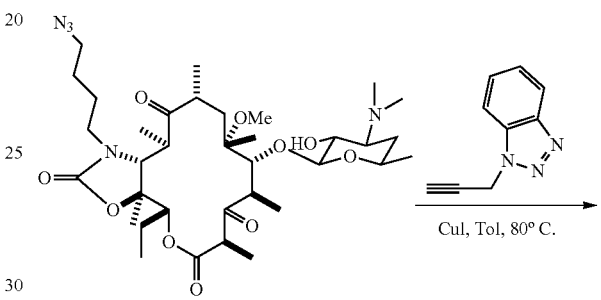

11-N-[4-(4-Benzotriazol-1-ylmethyl-[1,2,3]triazol-1-yl)-butyl]-6-O-methyl-5-O-dasosaminyl-3-oxo-erythronolide A, 11,12-carbamate. A mixture of 11-N-(4-Azido-butyl)-6-O-methyl-5-O-desosaminyl-3-oxo-erythronolide A, 11,12-carbamate (3 mg, 0.0039 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform: methanol plus 1% ammonium hydroxide) to give 3 mg of the desired compound. MS: $C_{44}H_{66}N_8O_{10}$ calculated M$^+$=866.5. Found: M+H$^+$867.5.

11-N-[4-(4-Benzotriazol-1-ylmethyl-[1,2,3]triazol-1-yl)-butyl]-6-O-methyl-5-mycaminosyl-3-oxo-erythronolide A, 11,12-carbamate. A mixture of 11-N-(4-azido-butyl)-6-O-methyl-5-mycaminosyl-3-oxo-erythronolide A, 11,12-carbamate (3 mg, 0.004 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform: methanol plus 1% ammonium hydroxide) to give 3 mg of the desired compound. MS: $C_{44}H_{66}N_8O_{11}$ calculated M$^+$=882.5. Found: M+H$^+$=883.5.

METHOD EXAMPLES

Example

Pivotal Efficacy of CEM-101 against a Lethal Inhalational *B. anthracis* Challenge in Cynomolgus Macaques evaluating the efficacy of CEM-101 against a lethal aerosol challenge. Forty-two (21 male, 21 female) naïve Cynomolgus macaques approximately 2.5-5.0 kg, ~2-5 years of age, (available from Covance) are tested (40 placed on study and 2 extras). Monkeys are tested and verified negative for tuberculosis and also prescreened within 30 days prior to receipt to confirm that they are seronegative for Simian Immunodeficiency Virus (SIV), Simian T-Lymphotrophic Virus-1 (STLV-1), and Cercopithecine herpesvirus 1 (Herpes B virus) and negative for Simian Retrovirus (SRV1 & SRV2) by PCR. See Table 7.

TABLE 7

| Proposed Study Design | | | | | | |
|---|---|---|---|---|---|---|
| Group ID | Monkeys/ Group | Antibiotic or Vehicle | Dose (mg/kg) | Dosing Regimen | Time to 1st Dose (hrs PC) | Treatment Duration (days) |
| 1 | 10 | CEM-101 | 5 | QD | 24 | 14 |
| 2 | 10 | CEM-101 | 10 | QD | 24 | 14 |
| 3 | 10 | CEM-101 | 15 | QD | 24 | 14 |
| 4 | 10 | Sterile Water for Injection | 2 mL/kg | QD | 24 | 14 |

Animals are weighed on study days −7 and 0. Monkeys that die or are euthanized on study are weighed prior to necropsy. Additional weights may be taken if an animal appears to be losing weight during the course of disease progression. Clinical observations of all monkeys performed twice daily during the pre-challenge period. Blood samples are taken from a femoral artery or vein, saphenous vein, or other appropriate vein on the days specified in Table 8. Blood samples collected on the day of challenge are collected prior to challenge. Body temperatures are monitored via an implantable programmable temperature transponder chip (such as the IPTT-300 BMDS, Seaford, Del.) twice a day starting at implantation (~day −7) through day 28.

TABLE 8

Blood Draw Schedule

| Time Point | Bacteremia (Culture) | CBC/CRP | Clinical Chem. | Antibiotic Level Det. | Coagulation Assay |
|---|---|---|---|---|---|
| Day −7 | | X | X | | X |
| Day 0 (prior to challenge) | | X | X | X | |
| 24 hours PC (Prior to treatment) | X | X | X | | X |
| 28 hours PC (~4 hours PT) | | | | X | |
| 48 hours PC | X | X | X | X | X |
| 72 hours PC | X | X | X | | X |
| 96 hours PC | X | X | X | | X |
| Day 7 (~4 hours PT) | X | X | X | X | X |
| Day 8 | | | | X | |
| Day 14 (~4 hours PT) | X | X | X | X | X |
| Day 15 | | | | X | |
| Day 21 | X | X | X | | X |
| Day 28 | X | X | X | | X |
| Day 30 | X | | | | |
| Day 32 | X | | | | |
| Terminal | X | CRP | | | |

PT = post-treatment,
PC = post-challenge

Monkeys are transported into the BL (biohazard laboratory level 3)~5-10 days prior to challenge to allow time for acclimation. Monkeys within each challenge day group are randomized for challenge order prior to challenge. On day 0, monkeys are anesthetized with Telazol (1-6 mg/kg, IM) and placed into a plethysmography chamber and a Class III cabinet system for the targeted challenge agent aerosolized by a Collison nebulizer and delivered via a head-only inhalation exposure chamber.

Aerosol concentrations of challenge material are quantified by determination of colony forming units (cfu). Effluent streams are collected directly from an animal exposure port by an in-line all-glass impinger. Serial dilutions of impinger samples are plated and counted.

Following challenge, monkeys are observed twice daily for a minimum of 28 days under BL-3 conditions for survival and clinical signs of illness. Surviving animals may be removed from the BL-3 after day 28 subsequent to demonstrating three consecutive negative blood cultures.

Blood samples from time points indicated in Table 8 are cultured to determine the presence or absence of bacteria. Hematology evaluation (CBC) is also conducted. CRP analysis is performed on residual plasma collected from each whole blood sample after processing. CRP analysis is also conducted on terminal blood samples collected in EDTA tubes if the plasma is able to be isolated. Coagulation assays include prothrombin time (PT), activated partial thromboplastin time (aPTT), fibrinogen, and D-dimer.

Statistical Analysis: Fisher's exact tests are used to compare survival rates between each antibiotic treatment group and the control group. A time-to-death analysis is performed on these data determining if there are differences in protection for the different groups based on a length of survival model. The Kaplan-Meier estimates of survival probabilities are plotted. The log-rank or Wilcoxon test or Cox proportional hazard regression are used to determine if there are significant differences between the groups, and if so, which groups are significantly different. Bacteremia culture data is analyzed separately at each time point Summary statistics with 95 percent confidence intervals are produced for each group and time point. Fisher's exact test is used to test whether there are any significant differences in the bacteremia culture data between groups. For hematology, clinical chemistry, coagulation, temperature, peak and trough antibiotic levels; summary statistics and 95% confidence intervals are produced for each group. Analysis of variance (ANOVA) models can be fitted to each parameter at each time point to determine if there are statistically significant differences between the treatment groups. Few control animals are expected to survive, baseline values for treated animals may be used in these comparisons, with each animal serving as its own control. Mean changes in temperature, clinical chemistry, and hematology parameters are compared to zero, to evaluate any change in health status.

Efficacy of CEM-101 against a Lethal Inhalational *F. tularensis*, *Y. pestis*, and *B. mallei* Challenge in NHPs and Pilot Efficacy of CEM-101 against a Lethal Inhalational *B. anthracis* Challenge in NHPs are determined using the methods described above.

Example

Rabbit Pharmacokinetics and Tolerability Study

TABLE 1

Groups

| Treatment Group | Product | No. of Animals per Sex (Total) | Dose Level (mg/kg) |
|---|---|---|---|
| 1 | CEM-101 | 5 (10) | 5 |
| 2 | CEM-101 | 5 (10) | 10 |
| 3 | CEM-101 | 5 (10) | 15 |
| 4 | Control | 5 (10) | NA |

TABLE 2

Blood Draw Schedule

| Time Point | Antibiotic Levels | Clinical Chemistry | Clinical Hematology |
|---|---|---|---|
| Day −7 | X | X | X |
| Day −3 | X | X | X |
| *1 hr | X | X | X |
| *2 hr | X | X | X |
| *4 hr | X | X | X |
| *6 hr | X | X | X |
| *12 hr | X | X | X |
| *18 hr | X | X | X |
| *24 hr | X | X | X |
| *48 | X | X | X |
| *72 | X | X | X |
| *96 | X | X | X |
| *Day 10 | X | X | X |

TABLE 2-continued

Blood Draw Schedule

| Time Point | Antibiotic Levels | Clinical Chemistry | Clinical Hematology |
|---|---|---|---|
| *Day 20 | X | X | X |
| *Day 30 | X | X | X |

*Blood draws collected post-treatment

Blood levels of CEM-10 are determined from blood samples collected from treated and control rabbits at the indicated time before and during administration of CEM-101.

Example

Pharmacokinetics (PK) in non-human primates. The PK data is collected in three phases. Eight monkeys (4 male, 4 female) participate in each phase (Table 3). Each phase is followed by a 7-day minimum washout period prior to initiation of the next phase.

TABLE 3

Study Design

| Phase | # per Phase | CEM-101 Dose (mg/kg) | Blood Collection |
|---|---|---|---|
| 1 | 8 | 5 | Day 1: $0^a$, 1, 2, 4, 6, 8, 12, 18, 24, 48 hr, 96 hr |
| 2 | 8 | 10 | Day 1: $0^a$, 1, 2, 4, 6, 8, 12, 18, 24, 48 hr, 96 hr |
| 3 | 8 | 15 | Day 1: $0^a$, 1, 2, 4, 6, 8, 12, 18, 24, 48 hr, 96 hr |

Example

Characterization of *Burkholderia mallei* Challenge Material and Delivery in the Large Animal Exposure system. The strain of *Burkholderia mallei* is streaked for isolation on appropriate growth media (such as Lysogeny broth (LB) agar with 4 percent glycerol or Ashdown's medium). Upon confirmation of colony purity and morphology (considering that morphologically variant colonies are common for *B. mallei*), all colonies are removed and suspended in an appropriate bacterial storage media and frozen at ≤−70° C. A collection of colonies are prepared rather than a single isolated colony (it is appreciated that isolating a single colony type may inadvertently select a variant with altered virulence properties). The collected colonies constitute the master cell bank. The procedure is repeated by streaking from the master cell bank to prepare the working cell bank.

All cultures prepared on agar media in the preparation of the master and working cell banks are examined for colony morphology and purity. Gross morphological examination includes descriptions of colony shape, size, elevation, margin, color, surface appearance, density, and consistency. If a cell bank is determined to contain contaminants, it is re-derived from the master or cell bank.

Culture material from master and working cell banks are Gram-stained. Gram-stain results and gross cellular morphology are observed and compared to previous results in the published literature. Working cell bank material is used to inoculate broth cultures; flasks are incubated for various times and the optical density of the cultures measured. Multiple broth cultures are prepared. Each culture is grown to a target optical density and then the numbers of CFU/mL of culture are determined by spread plate enumeration. A ratio of the number of CFU/mL is determined by averaging the results of multiple cultures for one culture density. Real-time qualitative PCR (+/−PCR) is performed to determine, at the nucleic acid level, that each working cell bank is indeed the *B. mallei* strain provided. The concentration of bacteria in the master and working cell banks for all strains is determined by spread plate enumeration, or comparable technique.

Fresh *B. mallei* suspensions are prepared from stock samples. A fresh batch is prepared for each day aerosol tests are conducted. Starting (nebulizer) *B. mallei* solutions for aerosolization diluted in sterile phosphate buffered saline (PBS) containing 0.01% (wt/vol) gelatin with 9.7% trehalose (wt/vol) (BSGT) and approximately 8 mL are placed into the nebulizer for each test. Aerosol samples are collected from the exposure chamber using glass impingers (e.g. model 7541 Ace Glass, Inc.) filled with ~20 mL of sterile phosphate buffered saline (PBS) containing 0.01% (wt/vol) gelatin (BSG) and 0.01% anti-foam A until plating for cfu counts. The aerosol particle size distribution are sampled from the exposure system and measured using an aerodynamic particle sizer.

A series of aerosol exposure system-characterization tests are performed to quantify the aerosol concentration of viable *B. mallei* (i.e. CFU) and the reproducibility of aerosol generation. Table 4 illustrates a test matrix that can be used to test for reproducibility of the aerosol system. The characterization tests are repeated to generate four different, targeted aerosol concentrations on each day for 3 days. The generation of each targeted aerosol concentration is repeated three times on each day. Aerosol samples are collected and enumerated for CFU via the spread plate technique. Additionally, the temperature, relative humidity, and aerosol particle size during each test is monitored for at least one time point.

TABLE 4

Aerosol Characterization Testing

| Test number | Target aerosol concentration (CFU/L air) | Number of test iterations per target aerosol concentration |
|---|---|---|
| Test 1 | A | 3 |
| Test 2 | B | 3 |
| Test 3 | C | 3 |
| Test 4 | D | 3 |

The complete test matrix (Tests 1-4) is repeated over 3 separate days.

For aerosol characterization testing, statistical ANOVA models are fitted to the test data for the aerosol system. These data consist of four aerosol concentrations tested three times on each day with the entire experiment repeated on three different days. A statistical hypothesis is tested for whether the measured system output (e.g., spray factor) is reproducible (i.e., not statistically significantly different on one day compared to another). A negative result (i.e., not statistically significant) will conclude reproducibility. Power analysis will also be performed to determine the minimum sensitivity of the test to identifying true differences Example Development of the mouse aerosol system for generation, delivery, and collection of *B. mallei*. A series of aerosol exposure system-characterization tests are performed to quantify the aerosol concentration of viable *B. mallei* (i.e.

CFU) and the reproducibility of the exposure system. Table 4 illustrates the proposed tentative test matrix that is used to test for reproducibility of the aerosol system. The characterization tests are repeated to generate four different, targeted aerosol concentrations on each day for 3 days. The generation of each targeted aerosol concentration is repeated three times on each day. Aerosol samples are collected as described above and enumerated for colony forming units (cfu) via a spread plate technique.

For aerosol characterization testing, statistical ANOVA models are fitted to the test data for the aerosol system. As described above, this data consists of four aerosol concentrations tested three times on each day with the entire experiment repeated on three different days. A statistical hypothesis is tested for whether the measured system output (e.g., spray factor) is reproducible (i.e., not statistically significantly different on one day compared to another). A negative result (i.e., not statistically significant) concludes reproducibility. Power analysis is also performed to determine the minimum sensitivity of the test to identifying true differences.

Example

Determining the Inhaled Median Lethal Dose ($LD_{50}$) of *B. mallei* in Mice. The determination of the inhaled $LD_{50}$ for *B. mallei* is conducted in phases. Each phase of this study consists of a post-challenge period which will extend to Day 28. The day an animal is challenged is designated as study Day 0. Phase I consists of 5 groups, phase II four groups and phases III and IV consist of three groups each. Based on the mortality results of the previous phases, new target exposure doses are determined. This phased approach allows for increased confidence in the inhaled $LD_{50}$ value.

TABLE 6

Phase Approach to Determine the $LD_{50}$ in Mice

| Phase | Groups per Phase | Total Mice |
|---|---|---|
| I | 5 groups of 4 | 20 |
| II | 4 groups of 8 | 32 |
| III | 3 groups of 8 | 24 |
| IV | 3 groups of 8 | 24 |

Mice are challenged via the inhalation route with *B. mallei* on Study Day 0 (for each Phase). A nose-only aerosol exposure system (for example a CH Technologies Tower) is utilized to deliver the desired aerosol doses to mice. The CH Technologies Tower system used for the mouse aerosol challenge testing is capable of exposing up to 30 mice at a time with the addition of impinger samplers, an aerosol particle size analyzer, temperature and humidity monitoring, and mass flow meters (MFM) and mass flow controllers (MFC) to control and/or monitor the aerosol flows. Briefly, forced air enters the system through high efficiency particulate air (HEPA) filters and is divided into a continuous air stream (continuous air) and an air stream that either flows into the Collison nebulizer (during aerosol generation) or by-passes it (between aerosol generations). MFC regulate the flow for each of the air streams. The *B. mallei* aerosol, created by the nebulizer, is mixed with continuous air before delivery to the exposure tower. The aerosol exposure parameters required to deliver these doses are based on results from the proposed mouse aerosol system characterization study described above.

Aerosol concentrations of *B. mallei* are quantified by determination of colony forming units (cfu). Effluent streams are collected directly from an animal exposure port by an in-line all-glass impinger. Serial dilutions of impinger samples are plated and enumerated.

The mice are observed twice daily for a total of 29 days, which includes Study Day 0 through Study Day 28, to determine the onset of clinical signs of disease and survivability.

For $LD_{50}$ (inhaled median lethal dose) determinations in mice, experiments are conducted in phases (Feder, 1992). Probit dose-response models are fitted to dose-lethality data for mice using the method of maximum likelihood (Finney, 1971 and Feder, 1991). Estimated parameters of the probit dose-response models are used to compute the $LD_{50}$. Fieller's method (Finney, 1971) or other appropriate methods are used to compute a 95 percent confidence interval for the $LD_{50}$.

Time to onset of each of the clinical signs are recorded until death, euthanasia, or end of the clinical observation period of the animal. The proportion of animals showing each of the clinical signs and the time to onset of each sign are determined. Mortality is recorded at the time observed. Cox proportional hazards models are fitted to the time to onset and time to death data, with dose as an explanatory variable. Because more severe signs may mask less severe signs, signs may be grouped for this analysis. The median time to signs and median time to death is calculated at the $LD_{50}$.

Example

Natural History/$LD_{50}$ Determination of Inhalational *Burkholderia mallei* Disease in Cynomolgus macaques. Determination of the lethal dose ($LD_{50}$) of *B. mallei* and characterization of the natural history of inhalational melioidosis in cynomolgus macaques is determined by monitoring clinical signs of disease including clinical observations, hematology, clinical chemistry, telemetric parameters, coagulation assays, bacteremia, and numbers of bacteria in selected organs.

Twenty two (11 male, 11 female) naïve cynomolgus macaques (monkeys, NHPs) that are approximately 2.5-5.0 kg (~2-5 years of age) are obtained (available from Covance). Two of the NHPs will serve as replacements, if necessary, during Phases I, II, and III. Monkeys are tested and verified negative for tuberculosis and also prescreened within 30 days prior to receipt to confirm that they are seronegative for Simian Immunodeficiency Virus (SIV), Simian T-Lymphotrophic Virus-1 (STLV-1), and Cercopithecine herpesvirus 1 (Herpes B virus) and negative for Simian Retrovirus (SRV1 & SRV2) by PCR. Monkeys are quarantined for a minimum of five weeks prior to being placed on study. Prior to placement on study all monkeys are surgically implanted with telemetry transmitters (for example, item D70-PCTP, purchased from Data Sciences International, DSI).

Ten groups of monkeys are exposed to various doses of *B. mallei* delivered via aerosol over a period of four phases (see Table 7). Based on the mortality results of the previous phases, new target exposure doses are determined for the succeeding phase. This phased approach allows for increased confidence in the estimated inhaled $LD_{50}$ value. The first three phases are used to determine the $LD_{50}$ of *B. mallei* in NHPs. In the final phase, the remaining 4 NHPs are challenged with a high exposure expected to be lethal in a majority of animals based on the results from the first three phases (i.e. target an exposure dose around the $LD_{90}$). If the replacement NHPs are not used in Phases I, II, or III, then they also are challenged in Phase IV. The information collected in Phase IV supports the natural history information collected in the first 3 phases and increases understanding of the disease progression in animals challenged with elevated doses similar to those which might be utilized in efficacy studies. Results obtained from Phase IV may also increase the precision of an $LD_{90}$ estimate.

TABLE 7

Phase Approach to Determine the $LD_{50}$ in Cynomolgus Macaques

| Phase | Group | CFU dose | Number of NHPs |
|---|---|---|---|
| I | 1 | 10,000 | 2 |
|  | 2 | 100,000 | 2 |
|  | 3 | 1,000,000 | 2 |
|  | 4 | 10,000,000 | 2 |
| II | 5 | TBD | 2 |
|  | 6 | TBD | 2 |
| III | 7 | TBD | 2 |
|  | 8 | TBD | 2 |
| IV* | 9 | TBD | 2 |
|  | 10 | TBD | 2 |

*Two additional NHPs are included in this phase if they are not used as replacements in Phases I, II, or III.

The animals are weighed during quarantine and on Study Days −7 and 0. Monkeys which die or are euthanized on study are weighed prior to necropsy. Additional weights may be taken if an animal appears to be losing weight during the course of disease progression. Clinical observations of all monkeys are performed twice daily during the pre-exposure period. Following aerosol exposure, monkeys are monitored three times daily for 28 days post-exposure for survival and clinical signs of illness: moribund, respiratory distress, appetite, activity (recumbent, weak, or unresponsive), seizures, and other clinical observations (described by observer).

Blood samples are taken from a femoral artery or vein, saphenous vein, or other appropriate vein on the days specified in Table 8. Blood samples collected on the day of exposure will take place prior to exposure.

Telemetry: Baseline and post-challenge data for body temperature; ECG; activity; and cardiovascular function (heart rate, systolic/diastolic pressure, pulse pressure, mean pressure, and respiratory pressure) are collected for at least 30 seconds every 15 minutes throughout the study. Baseline data are collected for at least 10 days prior to challenge. Details on the specific operation and data collection are contained in SOP BBRC.VI-087, SOP BBRC.VI-093, and SOP BBRC.VI-096.

TABLE 8

Natural History Blood Draw Schedule

| Time Point | Bacteremia | CBC/CRP | Clinical Chemistry | Coagulation Assays | QPCR |
|---|---|---|---|---|---|
| Day −7 | X | X | X | X | X |
| Day 0 |  | X | X | X |  |
| Day 1 PC | X | X | X | X | X |
| Day 2 PC | X | X | X | X | X |
| Day 3 PC | X | X | X | X | X |
| Day 4 PC | X | X | X | X | X |
| Day 5 PC | X | X | X | X | X |
| Day 6 PC | X | X | X | X | X |
| Day 7 PC | X | X | X | X | X |
| Day 14 PC | X | X | X | X | X |
| Day 21 PC | X | X | X | X | X |
| Day 28 PC | X | X | X | X | X |
| Terminal | X | CRP only |  |  | X |

Monkeys are transported into the BL-3~14 days prior to exposure to allow time for acclimation. On Day 0, monkeys are anesthetized with Telazol (1-6 mg/kg, IM) and placed into a plethysmography chamber and a Class III cabinet system and exposed to the targeted dose of B. mallei aerosolized by a Collison nebulizer and delivered via a head-only inhalation exposure chamber. Aerosol concentrations of B. mallei are quantified by determination of CFU. Effluent streams are collected directly from an animal exposure port by an in-line all-glass impinger. Serial dilutions of impinger samples are plated and enumerated.

Monkeys surviving the 28 day post-exposure period are euthanized and examined as described below. Because of the potential for surviving monkeys to develop a chronic infection, all animals must be euthanized In addition, the quantification of bacterial load in the tissues of animals in subsequent efficacy studies may provide a secondary endpoint for analysis (i.e. if the treatment doesn't significantly reduce mortality it may significantly reduce bacterial load).

Blood samples from time points indicated in Table 8 are cultured to determine the presence or absence of B. mallei. In addition, at each of these time points approximately 100 µl of whole blood is collected from which DNA is isolated and QPCR analysis performed.

Hematology evaluation (CBC) is conducted includes, but is not be limited to, the following parameters:

| | |
|---|---|
| White blood cell count (WBC) | Mean corpuscular volume (MCV) |
| Differential leukocyte(% and absolute) count | Mean corpuscular hemoglobin (MCH) |
| Neutrophil:Lymphocyte Ratio (N/L Ratio) | Mean corpuscular hemoglobin concentration |
| Hemoglobin (HGB) | Red cell distribution width (RDW) |
| Hematocrit (HCT) | Platelet count (PLT) |
| Red blood cell count (RBC) | Mean platelet volume (MPV) |

Clinical chemistry evaluation is conducted and l includes, but is not limited to, the following parameters:

| | |
|---|---|
| Alanine aminotransferase (ALT) | Albumin/Globulin (A/G) Ratio |
| Aspartate aminotransferase (AST) | Blood urea nitrogen (BUN) |
| Alkaline Phosphatase (ALP) | Creatinine |
| Gamma-Glutamyl Transferase (GGT) | BUN/Creatinine Ratio |
| Lactate dehydrogenase (LDH) | Glucose |
| Sorbitol Dehydrogenase (SDH) | Sodium |
| Total bilirubin | Potassium |
| Total protein | Chloride |
| Albumin | Calcium |
| Globulin | Phosphorus |

Blood samples for analysis of coagulation factors are collected into tubes containing sodium citrate. C-Reactive protein (CRP) analysis is performed on residual plasma collected from each whole blood sample after processing. CRP analysis is also conducted on terminal blood samples collected in EDTA tubes if the plasma can be isolated.

Gross necropsy is performed on all monkeys that die or are euthanized. Portions of target tissues including but not limited to lungs, spleen, and liver are homogenized, the DNA isolated, and qPCR performed to determine bacterial loads in these organs. Sections of target tissues including but not limited to brain, lungs, kidney, liver, spleen, mediastinal and bronchial lymph nodes as well as all gross lesions are preserved in 10% neutral buffered formalin. Histopathology is performed on all animals including survivors euthanized on study day 28.

Probit dose-response models are fitted to dose-lethality data for monkeys using the method of maximum likelihood (Finney, 1971 and Feder, 1991). Estimated parameters of the probit dose-response models are used to compute the $LD_{50}$ and $LD_{90}$. Fieller's method (Finney, 1971) or other appropriate methods are used to compute a 95 percent confidence interval for the $LD_{50}$ and $LD_{90}$.

Time to onset of each of the clinical signs is recorded until death, euthanasia, or end of the clinical observation period of the animal. The proportion of animals showing each of the clinical signs and the time to onset of each sign is determined. Cox proportional hazards models are fitted to the time to onset and time to death data, with dose as an explanatory variable. Because more severe signs may mask less severe signs, signs may be grouped for this analysis. The median time to signs of illness and median time to death are calculated at the $LD_{50}$ dose.

Statistical Analysis of Hematology, Clinical Chemistry, Coagulation and qPCR results: These parameters are evaluated relative to baseline for the same animal by calculating the shift from the mean pre-challenge level at each data collection time point. If necessary, hematology and clinical chemistry data are first transformed by the logarithm to produce a more normally distributed response. In this case, final results are returned to their original units through exponentiation. Summary statistics are provided for the data. At each time point, the mean shift from baseline for all animals is evaluated using t-tests to determine if the parameter shift is statistically significantly different than no shift. For each of the telemetry parameters, data collected immediately prior to challenge are averaged for each animal, resulting in baseline averages. Telemetry results in the post-challenge period are then adjusted for each animal by subtracting the baseline average. Further data smoothing may be employed by moving averages or other appropriate method. The time trend in the baseline adjusted and smoothed data measurements as well as the cumulative sum of adjustments for each telemetry parameter are plotted for all animals.

Specific criteria are established for onset of disease using the telemetry data. Statistical tests are determined to assess the specific time point for which a disease criterion occurs in some proportion of the population and/or provide a time interval around a certain mean manifestation of disease. Where possible and judged relevant, the additional data of time to death, hematology, bacteriology, and clinical observations may also be incorporated into this analysis to determine the optimum timing of initiation of therapy.

Example

Efficacy of CEM-101 against a Lethal Inhalational *F. tularensis, Y. pestis*, and *B. mallei* Challenge in BALB/c Mice.

TABLE 9

| Study Design | | | |
|---|---|---|---|
| Group | CEM-101 Dose (mg/kg) | Number of mice | Treatment Duration (days) |
| 1 | 50 | 20 | 14 |
| 2 | 100 | 20 | 14 |
| 3 | 150 | 20 | 14 |
| 4 | 200 | 20 | 14 |
| 5 | Control | 20 | 14 |

One hundred and ten (110) BALB/c mice are used in this procedure (100 to be placed on study and 10 extras). On day 0, mice are placed into a nose-only aerosol exposure system and exposed to agent aerosolized by a Collison nebulizer. Aerosol concentrations of agent are quantified by determination of colony forming units (cfu). Effluent streams are collected directly from an exposure port by an in-line all-glass impinger. Serial dilutions of impinger samples are plated and enumerated.

Following challenge, mice are observed twice daily for 28 days for survival and clinical signs of illness. The bacterial burden in the lungs, spleen and peripheral blood are determined by quantitative PCR from all mice found dead or euthanized. All animals surviving the 28 day post-challenge observation period are anesthetized, and a terminal blood sample is collected followed by immediate euthanasia. Following euthanasia a specimen of lung and spleen are also collected for bacterial burden analysis.

Fisher's exact tests are used to compare survival rates between each antibiotic treatment group and the control group. A time-to-death analysis are performed on these data to determine if there are differences in protection for the different groups based on a length of survival model.

Pilot Efficacy and Pivotal Efficacy of CEM-101 against a Lethal Inhalational *B. anthracis* Challenge in Rabbits (see general Rabbit efficacy study outline below).

Using the methods described above the efficacy of CEM-101 against inhalation challenge of rabbits with aerosolized of *B. anthracis*

TABLE 12

| Rabbit Post-Exposure Efficacy Studies (used for *B. anthracis*). | | | |
|---|---|---|---|
| Group | CEM-101 Dose (mg/kg) | Number of animals | Treatment Duration (days) | Hematology/Clinical Chemistry/Bacteremia Analysis (relative to the day of challenge) |
| 1 | 5 | 10 | 14 | −7, 1, 2, 3, 4, 7, 14, 21, 28 |
| 2 | 10 | 10 | 14 | −7, 1, 2, 3, 4, 7, 14, 21, 28 |
| 3 | 15 | 10 | 14 | −7, 1, 2, 3, 4, 7, 14, 21, 28 |
| 4 | Control | 10 | 14 | −7, 1, 2, 3, 4, 7, 14, 21, 28 |

Animals are treated between 18-24 hours post challenge. All animals are monitored for 28 days post challenge. Blood draws for CEM-101 peak and trough levels are collected after first, middle and last antibiotic treatment.

Example

MICs were determined by the microdilution method in 96-well plates according to Clinical and Laboratory Standards Institute (CLSI formally NCCLS) (1). Antibiotics were serially diluted twofold in 50 µl of cation-adjusted Mueller-Hinton broth (CAMHB). For *F. tularensis* determinations CAMHB was supplemented with 2% Isovitalex (Becton Dickinson). The antibiotic range was 16 to 0.008 µg/ml based on a final well volume of 100 µl after inoculation.

Inocula were prepared by suspending colonies from a 18-24 h (*B. anthracis, B. mallei* or *B. pseudomallei*) or 48 hr (*Y. pestis, F. tularensis*) sheep blood (SBA) or chocolate agar plate (according to CLSI). Suspended cultures were diluted with CAMHB to a bacterial cell density of $10^6$ CFU/ml. To each well of the 96-well plate, 50 µl of this dilution was added for a final inoculum of approximately $5 \times 10^4$ CFU/well. Plates were incubated at 35° C. MICs were determined visually at 24- and 48 h and by reading the plates at 600 nm (SpectroMax M2, Molecular Devices).

Inoculum preparation and antibiotic microdilution were performed according to CLSI methods. MICs of each agent were determined by the microdilution method in 96-well plates, after an 18- or 42-h incubation at 35° C., for 30 strains representing the genetic and geographic diversity of each bacterial species.

Quality control of antibiotic stocks was established by using *Staphylococcus aureus* ATCC 29213 and *Escherichia coli* ATCC 25922.

|  | # Strains | Range ug/ml | MIC50 ug/ml | MIC90 ug/ml |
|---|---|---|---|---|
| *B. anthracis* | 30 | <0.008-0.015 | <0.008 | <0.008 |
| *Y. pestis* | 30 | 0.25-2 | 1 | 2 |
| *F. tularensis* | 30 | <0.08-4 | 0.03 | 2 |
| *B. mallei* | 30 | 0.25-2 | 1 | 1 |
| *B. pseudomallei* | 30 | 16 | 16 | 16 |

Antibiotic susceptibility testing indicated that all of bacterial species in this study with the exception of *B. pseudomallei* are in therapeutically achievable ranges for CEM-101. *B. pseudomallei* has a demonstrated multi-drug efflux system that is active against macrolides(2) and the data indicating CEM-101 resistance are consistent. The *F. tularensis* distribution reflects overlap of the two distinct biovars "A" and "B" of this species. The B strains distribute to the higher MICs while the A strains distribute to the lower end. A strains are the more virulent and pose the greater BW/BT threat making their greater susceptibility fortuitous.

Since many of these bacterial agents are intracellular during infection the observed ability of many macrolides to preferentially accumulate in cells, may enhance efficacy among individuals exposed to aerosolized BW/BT agents. The demonstrated broad-spectrum activity against a variety of potential BW/BT bacterial agents along with oral bioavailability makes CEM-101 an attractive candidate for treatment after exposures and infections. Efficacy of CEM-101 in the animal-infection models for these agents should be evaluated.

Example

Human THP-1 macrophages were used. Accumulation was measured by microbiological assay. Intracellular activity was determined against phagocytized *S. aureus* (ATCC 25923; MICs: CEM-101, 0.125 mg/L; AZI, 0.5 mg/L) using a dose-response approach (AAC 2006; 50:841-51). Verapamil (100 µM) and gemfibrozil (250 µM) were used as inhibitors of P-glycoprotein and MRP, respectively (AAC, 2007; 51:2748-57).

Accumulations and activities after 24 h incubation, with and without efflux transporters inhibitors, are shown in the following Table, where Cc/Ce is the apparent cellular to extracellular concentration ratio, and $E_{max}$ is the maximal decrease of intracellular cfu compared to post-phagocytosis inoculum (calculated from non-linear regression [sigmoidal] of dose-effect response experiments).

|  | AZI | | | CEM-101 | | |
|---|---|---|---|---|---|---|
|  |  | Intracellular activity ($\Delta$ log cfu at 24 h) | | | Intracellular activity ($\Delta$ log cfu at 24 h) | |
| Condition | Cc/Ce [1] (24 h) | Static dose (mg/L) | $E_{max}$ [2] | Cc/Ce [1] (24 h) | Static dose (mg/L) | $E_{max}$ [2] |
| control | 127.7 ± 23.5 | ~7.0 | 0.10 ± 0.09 | 268.1 ± 7.1 | ~0.02 | −0.85 ± 0.23 [b] |
| Verapamil | 216.37 ± 46.6 [a] | ~0.2 | −0.37 ± 0.15 | 290.2 ± 12.9 | ~0.03 | −0.59 ± 0.22 [b] |
| Gemfibrozil | 129.12 ± 2.69 | ~3.8 | −0.12 ± 0.20 | 308.2 ± 47.8 | ~0.03 | −0.73 ± 0.20 [b] |

[a] Statistically significant from both control and Gemfibrozil;
[b] not statistically significant.

Example

Intracellular activity of antibiotics. The determination of antibiotic activity against intraphagocytic *S. aureus* strain ATCC 25923 was determined. Full dose-responses studies were performed to assess the impact of active efflux in the modulation of the intracellular activity of CEM-101 and AZI against intraphagocytic *S. aureus* (strain ATCC 25923 [MICs: CEM-101, 0.125 mg/L; AZI, 0.5 mg/L]. Antibiotics were compared at 24 h for: (i) their relative static concentration (Cs), and (ii) their relative maximal efficacy (E). While verapamil (but not gemfibrozil) increases the intracellular activity of AZI, neither inhibitor have significant effect on the activity of CEM-101, suggesting that the latter, in contrast with AZI, is not a substrate of the corresponding eukaryotic transporters.

Example

Cellular accumulation of antibiotics. The cellular content in macrolides was measured in THP-1 macrophages by microbiological assay, using *S. aureus* ATCC 25923 as test organism. Cell proteins was assayed in parallel using the Folin-Ciocalteu/Biuret method. The cell associated content in macrolides was expressed by reference to the total cell protein content, and converted into apparent concentrations using a conversion factor of 5 µL per mg of cell protein (as commonly used for cultured cells).

The cellular accumulation of CEM-101 in comparison with that of AZI in THP-1 cells was first measured FIG. 7 (panel A). At 24 h, both antibiotics concentrate to large extents in cells, but with a larger value (Cc/Ce) for CEM-101. In a second stage, whether CEM-101 is a substrate of Pgp or MRP efflux transporters was investigated FIG. 7 (panel B). Using a Pgp (verapamil) or MRPs inhibitor (gemfibrozil), no significant variations of the cellular accumulation of CEM-101 are observed while verapamil increases significantly the cellular accumulation of AZI.

Uptake of CEM-101 was linear over time, reaching accumulation levels about 375-fold within 24 h (AZI, 160X, CLR, 30X, TEL, 21X). Accumulation was suppressed by acid pH or addition of the proton ionophore monensin, but not modified by verapamil or gemfibrozil (preferential inhibitors of Pgp and MRP, respectively). Panel B shows that the accumulation of both CEM-101 and AZI was reduced when the experiments were conducted at acidic pH, with the change occurring almost entirely when the pH was brought from 7 to 6. Panel C shows that monensin, which is known to decrease the cellular accumulation of many weak organic bases, also almost completely suppressed the accumulation of both CEM-101 and AZI. In contrast, verapamil, an inhibitor of the P-glycoprotein efflux transporter (Pgp, also known as MDR1), increased the accumulation of AZI without affecting that of CEM-101, whereas gemfibrozil, an inhibitor of multidrug resistance proteins (MRP) and other organic anion transporters did not affect either compound. Neither verapamil nor gemfibrozil affected the accumulation of TEL or CLR (data not shown). The efflux of CEM-101 from cells incubated with 10 mg/L of CEM-101 for 1 h and then transferred into drug-free medium was examined Efflux proceeded in a bimodal fashion, with half of the cell-associated drug being released within approximately 10 min, followed by a slower release phase of several hours (data not shown).

Example

Macrolides accumulate in eukaryotic cells and are considered advantageous for the treatment of intracellular infections. Ketolides are active against erythromycin-resistant organisms. The cellular accumulation and intracellular activity of CEM-101 towards the intracellular forms of *Staphylococcus aureus* (S. a.), *Listeria monocytogenes* (L. m.), and *Legionella pneumophila* (L. p.) in comparison with AZI, CLR, and TEL is shown in the following table.

|  | MIC[a] | Cs[b] | $E_{max}$[c] |
|---|---|---|---|
| CEM-101 | | | |
| S.a. | 0.06 | 0.022 | −0.86 |
| L.m. | 0.004 | 0.11 | −0.66 |
| L.p. | 0.004 | 0.018 | −1.03 |
| AZI | | | |
| S.a. | 0.5 | >50 | 0.04 |
| L.m. | 1 | 11.6 | −0.81 |
| L.p. | 0.016 | 2.90 | −0.83 |
| CLR | | | |
| S.a. | 0.5 | 0.84 | −0.18 |
| L.m. | | | |
| L.p. | 0.007 | 0.12 | −0.71 |
| TEL | | | |
| S.a. | 0.25 | 0.63 | −0.29 |
| L.m. | | | |
| L.p. | 0.007 | 0.06 | −0.63 |

[a] mg/L;
[b] static concentration (mg/L) at 24 h;
[c] Δ log₁₀ CFU at 24 h compared to the post-phagocytosis inoculum Example MICs and extracellular activities of antibiotics were determined in MHB at both neutral and acidic pH. Intracellular activity was determined against *S. aureus* (ATCC 25923) phagocytosed by THP-1 macrophages as previously described (AAC, 2006, 50:841-851). Results were expressed as a change of efficacy compared to time 0 h.

| Conditions | CEM-101 | AZI | CLR | TEL |
|---|---|---|---|---|
| MICs (mg/L) | | | | |
| (i) pH 7.4 | 0.125 | 0.5 | 0.5 | 0.5 |
| (ii) pH 5.5 | 1-2 | 256 | 16 | 8 |
| Extracellular activity (24 h): Δ log cfu from time 0 h | | | | |
| (i) Broth pH 7.4 | | | | |
| Emax[1] | −1.4 ± 0.1 | −1.2 ± 0.6 | −1.4 ± 0.2 | −1.0 ± 0.4 |
| Static dose[2] | ∼0.06 | ∼3.63 | ∼1.41 | ∼0.28 |
| $R^2$ | 0.964 | 0.860 | 0.965 | 0.868 |
| (ii) Broth pH 5.5 | | | | |
| Emax[1] | −1.6 ± 0.4 | +2.1 ± 0.1 | −1.5 ± 0.8 | −1.4 ± 0.9 |
| Static dose[2] | ∼1.48 | / | ∼10.47 | ∼9.33 |
| $R^2$ | 0.915 | / | 0.911 | 0.879 |
| Intracellular activity (24 h): Δ log cfu from time 0 h | | | | |
| Emax[1] | −0.8 ± 0.2 | 0.10 ± 0.0 | −0.1 ± 0.1 | −0.4 ± 0.2 |
| Static dose[2] | ∼0.02 | ∼7.8 | ∼0.98 | ∼0.23 |
| $R^2$ | 0.906 | 0.980 | 0.974 | 0.935 |
| THP-1 | | | | |
| Emax[1] | −0.8 ± 0.2 | 0.1 ± 0.1 | −0.1 ± 0.1 | −0.4 ± 0.1 |
| Static dose[2] | ∼0.02 | ∼10 | ∼0.98 | ∼0.28 |

[1] Maximal decrease of intracellular cfu compared to initial, post-phagocytosis inoculum (calculated from non-linear regression [sigmoidal] of dose-effect response) run in broth (extracell.) or with infected macrophages (intracell.)
[2] Extracellular concentration (Cs in mg/L) yielding an apparent static effect. Comparative pharmacological descriptors (Emax and static concentrations [Cs]) obtained from the dose-responses studies. Dose-response studies in Mueller-Hinton broth. Against *S. aureus* ATCC 25923 and in broth, at pH 7.4, CEM-101 is systematically more active than AZI, CLR and TEL; at pH 5.5, AZI, CLR and TEL show significant decrease of their potencies, while CEM-101 shows less change.

Compared to AZI, CLR and TEL, CEM-101 activity was less affected by acidic pH of the broth and showed greater potency (lower static dose) and larger maximal efficacy (Emax) against intracellular *S. aureus*.

Example

Cell lines. Experiments were performed with THP-1 cells (ATCC TIB-202; American Tissue Culture Collection, Manassas, Va.), a human myelomonocytic cell line displaying macrophage-like activity (see, e.g., Barcia-Macay et al., Antimicrob. Agents Chemother. 50:841-851 (2006)). Assay of the cell-associated macrolides and calculation of the apparent cellular-to-extracellular-concentration ratios. Macrolides were assayed by a microbiological method, using *S. aureus* ATCC 25923 as a test organism. Cell proteins were measured in parallel using the Folin-Ciocalteu/biuret method. The cell-associated contents in macrolides were expressed by reference to the total cell protein content and converted into apparent concentrations using a conversion factor of 5 μL per mg of cell protein, an average value found for many cultured cells.

Bacterial strains, susceptibility testing, and 24-h dose-response curve studies with broth. *S. aureus* ATCC 25923 (methicillin [meticillin] sensitive), *L. monocytogenes* strain EGD, and *L. pneumophila* strain ATCC 33153 were used in the present study. MIC determinations were performed in Mueller-Hinton broth (for *S. aureus*) and tryptic soy broth (for *L. monocytogenes*) after a 24-h incubation, or in a-ketoglutarate-buffered yeast extract broth (for *L. pneumophila*) after a 48-h incubation. For *S. aureus* studies, 24-h concentration-response experiments in acellular medium were performed in Mueller-Hinton broth.

Cell infection and assessment of antibiotic intracellular activities. Infection of THP-1 cells and assessment of the intracellular activity of antibiotics were performed using conventional methods for *S. aureus* and *L. monocytogenes* or with minor adaptations for *L. pneumophila* using (i) a multiplicity of infection of 10 bacteria per macrophage and (ii) gentamicin (50 mg/liter) for 30 to 45 min for the elimination of nonphagocytosed bacteria.

Statistical analyses. Curve-fitting statistical analyses were performed with GraphPad Prism version 4.03 and GraphPad Instat version 3.06 (GraphPad Software, San Diego, Calif.).

Example

Figure 3:
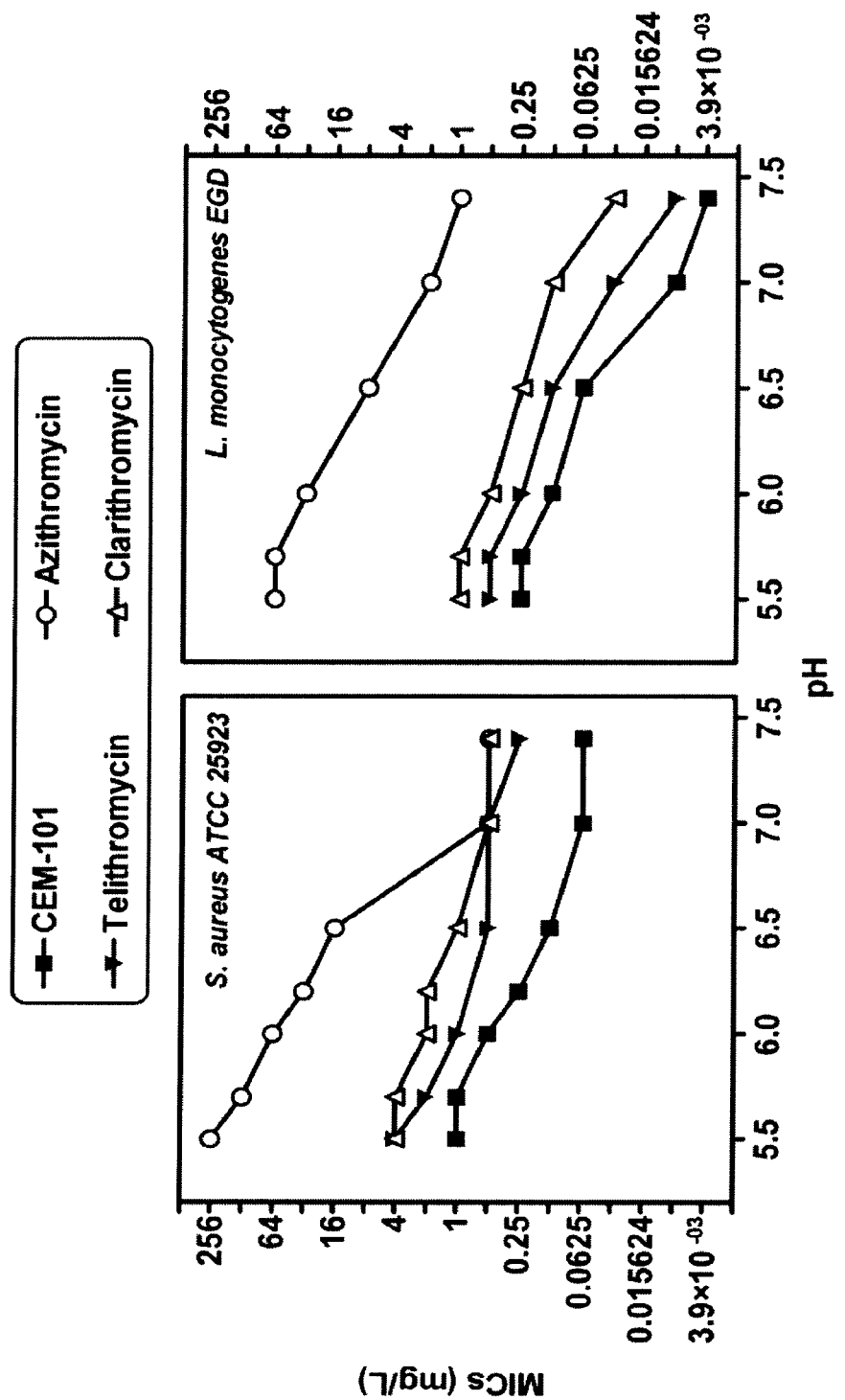

Susceptibility toward *S. aureus* ATCC 25923, *Listeria monocytogenes* EGD, and *Legionella pneumophila* ATCC 33153. CEM-101 showed lower MICs than AZI against the three selected organisms (*S. aureus*, 0.06 and 0.5 mg/liter; *L. monocytogenes*, 0.004 and 1 mg/liter; and *L. pneumophila*, 0.004 and 0.016 mg/liter) in conventional susceptibility testing. The MICs of CEM-101, TEL, AZI, and CLR against *S. aureus* and *L. monocytogenes* were measured in broths adjusted to pH values ranging from 5.5 to 7.4. The range was selected to cover the values at which the antibiotics could be exposed in the extracellular milieu or intracellularly for the two organisms considered. As illustrated in FIG. 3, all four drugs showed a marked decrease in potency against both organisms when the pH was decreased from 7.4 to 5.5, with AZI demonstrating the most significant loss of activity. CEM-101 retained the most activity, consistently showing the lowest MICs throughout the entire pH range investigated, with values (mg/liter) ranging from 0.06 (pH 7.4) to 0.5 (pH 5.5) for *S. aureus* (ATCC 25923) and 0.0039 (pH 7.4) to 0.25 (pH 5.5) for *L. monocytogenes* (EDG). For *L. pneumophila* (data not shown), the MIC of CEM-101 increased from 0.005 to 0.01 and that of AZI from approximately 0.01 to 0.25 mg/liter when the pH of the broth was decreased from 7.4 to 6.5 (no determination could be made at lower pH values because of absence of growth).

Example

Time and concentration effects against extracellular and intraphagocytic *S. aureus*. Short-term (6-h) time-kill curves were obtained for CEM-101 in comparison with those for AZI against *S. aureus* (ATCC 25923) in broth and after phagocytosis by THP-1 macrophages using two single fixed concentrations of 0.7 and 4 mg/liter. The lower concentration was chosen to be relevant to the serum concentration of AZI and CEM-101, and the higher concentration was selected to be above the MIC of AZI for the organisms of interest. Results presented in FIG. 5 show that under these conditions, only CEM-101 was able to significantly decrease CFU in broth as well as in THP-1 macrophages at the 0.7-mg/liter concentration. At the 4-mg/liter concentration in broth, AZI eventually achieved the same antibacterial effect as CEM-101, but at a lower rate (5 h compared to 1 h). In THP-1 macrophages, no consistent activity was detected for AZI, even at the 4-mg/liter concentration, whereas CEM-101 again achieved a reduction of approximately 1.5 log 10 CFU, similar to the magnitude seen at the 0.7-mg/liter concentration. In all situations with CEM-101, the maximal decrease of CFU was obtained within 1 h and was maintained thereafter.

Figure 4:
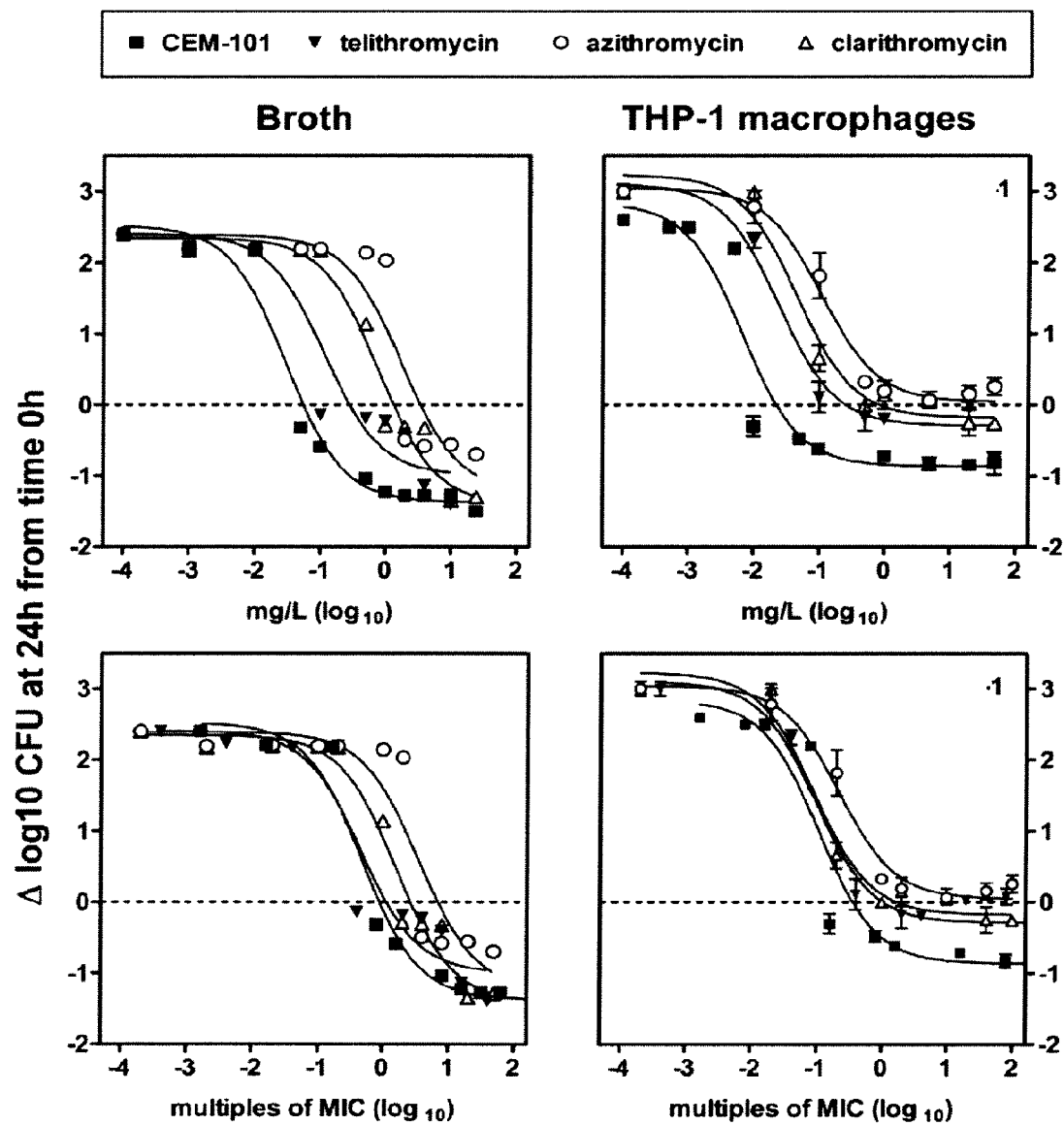
FIG. 4. Short-term time-kill effect of CEM-101 and AZI on *S. aureus* (ATCC 25923) in broth (left panels; pH 7.4) or after phagocytosis by THP-1 macrophages (right panels).

We then performed concentration-response experiments at a fixed time point (24 h) to obtain the pertinent pharmacological descriptors of CEM-101 activity (relative potency [50% effective concentration $\{EC50\}$], apparent static concentration $[C_s]$, and relative maximal efficacy $[E_{max}]$ in comparison with CLR, AZI and TEL activity (additional details are described in Barcia-Macay et al., Pharmacodynamic evaluation of the intracellular activities of antibiotics against *Staphylococcus aureus* in a model of THP-1 macrophages Antimicrob. Agents Chemother. 50:841-851 (2006)). Data are presented in FIG. 4 as a function of (i) weight concentrations (mg/liter) and (ii) multiples of the MICs (as determined in broth at pH 7.4). The numerical values of the corresponding pharmacological descriptors are shown in the Table. Pertinent regression parametersa (with confidence intervals [CI]), and statistical analysis of the dose-response curves illustrated in FIG. 4.

| antibiotic | $E_{max}$* (CI) | | broth+ $EC_{50}$◊ (CI) | $C_s$◊◊ | $R^2$ |
|---|---|---|---|---|---|
| CEM-101 | −1.37 (−1.67 to −1.08) a; A | mg/L | 0.03 (0.02 to 0.06) a; A | 0.06 | 0.973 |
| | | x MIC | 0.48 (0.26 to 0.91) a; A | 0.88 | |
| TEL | −1.00 (−1.78 to −0.22) a; A | mg/L | 0.12 (0.03 to 0.52) b; A | 0.29 | 0.892 |
| | | x MIC | 0.46 (0.11 to 2.06) a; A | 0.96 | |
| AZI | −1.23 (−2.55 to 0.083) a; A | mg/L | 1.78 (0.45 to 7.02) c; A | 3.4 | 0.872 |
| | | x MIC | 3.55 (0.90 to 14.0) b; A | 6.87 | |
| CLR | −1.41 (−1.95 to −0.87) | mg/L | 0.80 (0.41 to 1.56) | 1.32 | 0.956 |

-continued

|  | a; A | x MIC | c; A<br>1.59<br>(0.81 to 3.1)<br>a, b; A | 2.65 |  |
|---|---|---|---|---|---|

| | THP-1 macrophages[++] | | | | |
|---|---|---|---|---|---|
| antibiotic | $E_{max}$[♦] (CI) | | $EC_{50}$[◊] (CI) | $C_s$[◊◊] | $R^2$ (CI) |
| CEM-101 | −0.86<br>(−1.36 to −0.37)<br>a; B | mg/L | 0.0068<br>(0.0023 to 0.020)<br>a; B | 0.022 | 0.927 |
| | | x MIC | 0.11<br>(0.037 to 0.32)<br>a; B | 0.35 | |
| TEL | −0.29<br>(−0.70 to 0.12)<br>b; B | mg/L | 0.024<br>(0.007 to 0.088)<br>b; B | 0.63 | 0.954 |
| | | x MIC | 0.097<br>0.027 to 0.35<br>a; B | 1.04 | |
| AZI | 0.04<br>(−0.23 to 0.32)<br>b; B | mg/L | 0.11<br>(0.05 to 0.22)<br>c; B | >50 | 0.983 |
| | | x MIC | 0.22<br>0.11 to 0.45<br>a; B | >100 | |
| CLR | −0.18<br>(−0.52 to 0.16)<br>b; B | mg/L | 0.046<br>(0.018 to 0.12)<br>b, c; B | 0.84 | 0.974 |
| | | x MIC | 0.093<br>0.035 to 0.25<br>a; B | 1.68 | |

[a]using all data points shown in FIG. 6 (data from samples without antibiotic when the extracellular concentration of an antibiotic is lower than 0.01 x MIC (5)
[+]original inoculum [time = 0 h]: 0.97 ± 0.24 × 10$^6$ CFU/mL (n = 3)
[++]original (post-phagocytosis) inoculum [time = 0 h]: 2.74 ± 0.55 × 10$^6$ CFU/mg protein (n = 3)
[♦]CFU decrease (in log$_{10}$ units) at time = 24 h from the corresponding original inoculum, as extrapolated for antibiotic concentration = ∞; samples yielding less than 5 counts were considered below detection level.
[◊]concentration (in mg/L or in x MIC) causing a reduction of the inoculum half-way between initial ($E_0$) and maximal ($E_{max}$) values, as obtained from the Hill equation (using a slope factor of 1);
[◊◊]concentration (in mg/L or in x MIC) resulting in no apparent bacterial growth (number of CFU identical to the original inoculum), as determined by graphical intrapolation; Statistical Analyses. Analysis of the differences between antibiotics (per column for the corresponding rows; one-way ANOVA with Tuckey test for multiple comparisons between each parameter for all drugs): figures with different lower case letters are significantly different from each other (p < 0.05). Analysis of the differences between broth and THP-1 macrophages (per row for the corresponding columns; unpaired, two-tailed t-test): figures with different upper case letters are significantly different from each other (p < 0.05).

The activities in both broth and THP-1 macrophages developed in a concentration-dependent fashion, as denoted by the sigmoidal shape of each best-fit function (Hill equation). In broth, the relative efficacy of CEM-101 ($E_{max}$ of −1.37 log$_{10}$) was similar to that of the other drugs ($E_{max}$ values of −1.00 to −1.41 log$_{10}$). In THP-1 macrophages, the relative efficacy of CEM-101 was significantly decreased compared to that in broth ($E_{max}$ of −0.86 log$_{10}$), but not to the same extent as those of the other drugs, which essentially became bacteriostatic only ($E_{max}$ values of 0.04 to −0.29 log$_{10}$). On a weight basis, CEM-101 had higher relative potencies (lower $E_{50}$ values) and lower static concentrations (lower $C_s$ values) than all three comparator drugs in both broth and in THP-1 macrophages. When the data were analyzed as a function of equipotent concentration (multiples of the MIC), these differences in $EC_{50}$ values were reduced, indicating that the MIC was the main driving parameter in this context. In broth, even when analyzed as multiples of the MIC, CEM-101 and CLR still showed significantly lower $EC_{50}$s than TEL and AZI.

Example

Activity against intraphagoctic L. monocytogenes and L. pneumophila. The same approach was used as that for S. aureus to assess the activities of CEM-101 and AZI against phagocytized L. monocytogenes and L. pneumophila to obtain information on concentration-effect relationships and on the corresponding pertinent pharmacological descriptors. As shown in FIG. 6, a relationship compatible with the Hill equation was observed in all cases, although the limited growth of L. pneumophila made the fitting of functions somewhat more uncertain. When the data were plotted against weight concentration, it appeared that CEM-101 had a higher relative potency (lower EC50) than AZI for both L. monocytogenes and L. pneumophila. This difference was reduced but nevertheless remained significant when data for L. pneumophila were plotted against multiples of the MIC, indicating that the MIC was an important but not the exclusive driver of intracellular activity against this organism. Conversely, no difference in the responses was seen for L. monocytogenes when data were expressed as multiples of the MIC. Numerical values of the pertinent pharmacological descriptors and statistical analysis of their differences are shown in the Table.

Pertinent regression parameters[a] (with confidence intervals [CI]), and statistical analysis of the dose-response curves illustrated in FIG. 6.

| antibiotic | $E^{max}$[♦] (CI) | | $EC_{50}$[◇] (CI) | $C_S$[◇◇] | $R^2$ |
|---|---|---|---|---|---|
| *L. monocytogenes* EGD[+] | | | | | |
| CEM-101 | −0.66 (−1.28 to −0.037) a | mg/L | 0.020 (0.005 to 0.073) A | 0.11 | 0.934 |
| | | X MIC | 5.00 (1.36 to 18.5) A | 0.88 | |
| AZI | −0.81 (−2.11 to 0.48) a | mg/L | 2.66 (0.91 to 7.73) B | 11.6 | 0.953 |
| | | X MIC | 2.66 (0.81 to 3.1) A | 11.6 | |
| *L. pneumophila* ATCC 33153[++] | | | | | |
| antibiotic | $E_{max}$[♦] (CI) | | $EC_{50}$[◇] (CI) | $C_S$[◇◇] | $R^2$ |
| CEM-101 | −1.03 (−1.34 to −0.72) a | mg/L | 0.052 (0.012 to 0.23) A | 0.018 | 0.920 |
| | | x MIC | 13.1 (3.02 to 57.0) A | 4.56 | |
| AZI | −0.83 (−2.00 to 0.34) a | mg/L | 2.86 (0.17 to 48.6) B | 2.90 | 0.903 |
| | | x MIC | 179.0 (10.5 to 3038) B | 181 | |

[a] using all data points shown in FIG. 6 (data from samples without antibiotics were not used because of evidence of extracellular growth when the extracellular concentration of an antibiotic is lower than 0.01 x MIC (5).
[+] original (post-phagocytosis) inoculum [time = 0 h; CFU/mg protein]): *L. monocytogenes*, 1.67 ± 0.22 × 10[6] (n = 3); *L. pneumophila*, 0.94 ± 0.60 × 10[6].
[♦] CFU decrease (in logo units) at time = 24 h (*L. monocytogenes*) or 48 h (*L. pneumophila*) from the corresponding original inoculum, as extrapolated for antibiotic concentration ∞; samples yielding less than 5 counts were considered below detection level.
[◇] concentration (in mg/L or in x MIC) causing a reduction of the inoculum half-way between initial ($E_0$) and maximal ($E_{max}$) values, as obtained from the Hill equation (using a slope factor of 1).
[◇◇] concentration (in mg/L or in x MIC) resulting in no apparent bacterial growth (number of CFU identical to the original inoculum), as determined by graphical intrapolation. Statistical analyses: analysis of the differences between the two antibiotics (per column for the corresponding rows; unpaired, two-tailed t-test): figures with different lower case letters are significantly different from each other ($p < 0.05$).

Example

Dose-response studies in infected THP-1 macrophages Against intraphagocytic *S. aureus* ATCC 25923, CEM-101 is more potent than AZI, CLR and TEL (lower Cs), In addition, CEM-101 is able to reduce the intracellular inoculum ($E_{max}$ ~1 log), which is not observed with any of AZI, CLR and TEL.

CEM-101 Uptake within Cells (ii): Role of the Cell Type

| Cells | THP-1 (human macrophages) | J774 (murine macrophages) | MDCK (canine epith. cells) | MDCK sur-expressing the MDR1 efflux transporters |
|---|---|---|---|---|
| Cc/Ce at 5 h | ~50-150 | ~60 | ~45 | ~30 |

Example

Example Dose-response studies of CEM-101 vs. comparators (AZI, CLR and TEL) against intracellular *S. aureus* ATCC 25923 (THP-1 macrophages). See FIG. 9 and the Table.

| | CEM-101 | AZI | CLR | TEL |
|---|---|---|---|---|
| Emax | −0.80 ± 0.11 | 0.04 ± 0.11 | −0.18 ± 0.13 | −0.29 ± 0.16 |
| Cs (mg/L) | ~0.01 | >50 | ~0.86 | ~0.27 |

Example

Intracellular activity: comparative studies with other anti-staphylococcal agents. Comparative dose-static response of antibiotics against intracellular *Staphylococcus aureus* (strain ATCC 25923) in THP-1 macrophages were measured. See FIG. 8 bars represent the MICs (in mg/L) or the extracellular static dose.

METHOD. Mouse peritoneal macrophages were infected with viable *M. leprae*, the drugs are added and incubated at 33° C. for 3 days. After 3 days macrophages were lysed to release the intracellular *M. leprae* which were then assayed for viability by radiorespirometry and viability staining. CEM-101 shows efficacy against intracellular *M. leprae* viability.

The Thai-53 isolate of *M. leprae*, maintained by serial passages in athymic nu/nu mice footpads, was used for all experiments. For axenic testing freshly harvested viable *M. leprae* were incubated in medium along with different concentrations of the drugs (CEM-101, CLR and rifampin) for 7 days at 33° C. At the end of this incubation drug-treated *M. leprae* were subjected to radiorespirometry to assess viability based on oxidation of palmitate and staining with viability dyes to assess the extent of membrane damage. For intracellular testing peritoneal macrophages from Swiss mice were infected with freshly harvested viable *M. leprae* at an MOI of 20:1 for 12 hours. At the end of the infection extracellular bacteria were washed and drugs added at different concentrations and incubated for 3 days at 33° C. At the end of 3 days cells were lysed to obtain the intracellular *M. leprae* for radiorespirometry and viability staining.

CEM-101 at 0.15 μg/ml was able to significantly (P<0.001) reduce the viability of *M. leprae* in both axenic and intracellular cultures when compared to controls Inhibition by CEM-101 was not statistically different from inhibition obtained with CLR under identical conditions and at the same concentration.

Example

The high potency of CEM-101 against *Streptococcus pneumoniae*, β-haemolytic and viridans group streptococci, *Staphylococcus* spp. and enterococci has been documented in early screening studies performed using reference Clinical and Laboratory Standards Institute (CLSI) methods. Since mechanisms and occurrences of resistance are increasing rapidly that may compromise the MLSB-ketolide class, the bactericidal activity (MBC and killing curves) of CEM-101 with five selected classes of antimicrobial agents when testing wild type (WT) and phenotypically/genotypically defined resistant organism subsets was assessed. MBC determinations for CEM-101, TEL, and CLR used CLSI methods for 40 strains (6 species groups). KC used 8 strains (6 species groups). PAE was tested (5 strains) at 4× concentration for 1 or 2 hours exposure; TEL control.

MBC and killing curve studies: A total of 40 strains (10 *S. pneumoniae*, 10 *S. aureus*, and 5 each of β-haemolytic streptococci, viridans group streptococci, coagulase-negative staphylococci [CoNS] and enterococci) were MIC tested followed by MBC determinations using CLSI procedures (MIC and MBC range, 0.008-16 μg/ml). The lowest concentration of a tested agent that killed ≥99.9% of the initial inoculum was defined as the MBC endpoint (Tables 2 and 3). Time kill bactericidal activity was performed for CEM-101, TEL, CLR, and AZI on eight selected strains according to methods described by Moody & Knapp, NCCLS M21-A3 and M26-A. The compounds were tested at 2×, 4×, 8X MIC; and colony counts were performed at T0, T2, T4, T8 and T24.

CEM-101 exhibited low MBC/MIC ratios (≤4) for BSA, SA and coagulase-negative staphylococci; and 2-fold greater potency than TEL. SA, enterococci and some macrolide/CLN-resistant (R) strains had higher ratios. KC results showed more rapid and greater cidal activity (concentration dependant) for CEM-101 compared to TEL. CEM-101 exhibited cidal activity against several Gram-positive species at rates and an extent greater than TEL.

Distribution of Isolates According to MBC/MIC Ratio for CEM-101, TEL, CLR and AZI

| Organism/Antimicrobial agent (no. tested) | No. of strains with MBC/MIC value of: | | | | | |
|---|---|---|---|---|---|---|
| | 1 | 2 | 4 | 8 | 16 | ≥32 |
| *S. pneumoniae* (10) | | | | | | |
| CEM-101 | 3 | 5 | 0 | 0 | 0 | 2 |
| Telithromycin | 2 | 6[a] | 0 | 0 | 0 | 2 |
| Clarithromycin | 2 | 3 | 1 | 0 | 0 | —[b] |
| Azithromycin | 2 | 4 | 0 | 0 | 0 | —[b] |
| β-haemolytic *streptococci* (5) | | | | | | |
| CEM-101 | 0 | 1 | 2 | 0 | 0 | 2 |
| Telithromycin | 0 | 1 | 1 | 1 | 0 | 2 |
| Clarithromycin | 0 | 0 | 1 | 1 | 0 | 2[b] |
| Azithromycin | 0 | 0 | 0 | 0 | 2 | 2[b] |
| Viridans group *streptococci* (5) | | | | | | |
| CEM-101 | 3 | 0 | 1 | 0 | 0 | 1 |
| Telithromycin | 2 | 1 | 1 | 0 | 0 | 1 |
| Clarithromycin | 0 | 0 | 1 | 0 | 0 | 3[b] |
| Azithromycin | 0 | 0 | 0 | 0 | 1 | 3[b] |
| *S. aureus* (10) | | | | | | |
| CEM-101 | 1 | 0 | 0 | 0 | 1 | 8 |
| Telithromycin | 0 | 0 | 0 | 0 | 0 | 10 |
| Clarithromycin | 0 | 0 | 0 | 0 | 0 | 6[b] |
| Azithromycin | 0 | 0 | 0 | 0 | 0 | 6[b] |
| Coagulase-neg. *staphylococci* (5) | | | | | | |
| CEM-101 | 1 | 1 | 0 | 3 | 0 | 0 |
| Telithromycin | 0 | 0 | 0 | 0 | 2 | 3 |
| Clarithromycin | 0 | 0 | 0 | 0 | 0 | 4[b] |
| Azithromycin | 0 | 0 | 0 | 0 | 0 | 4[b] |
| *Enterococcus* spp. (5) | | | | | | |
| CEM-101 | 0 | 0 | 0 | 0 | 0 | 5 |
| Telithromycin | 0 | 0 | 0 | 0 | 0 | 5 |
| Clarithromycin | 0 | 0 | 0 | 0 | 0 | 2[b] |
| Azithromycin | 0 | 0 | 0 | 0 | 0 | 2[b] |

[a]Includes six isolates with a MIC of ≤0.008 μg/ml and a MBC of 0.015 μg/ml (off scale comparisons).
[b]MBC was not evaluated on isolates with resistant level MIC results.

CEM-101 showed rapid bactericidal activity (reduction of ≥3 log 10 CFU/ml) against macrolide-susceptible strains of *S. aureus*, *S. epidermidis*, *S. pneumoniae*, *S. pyogenes* (only at 8×MIC) and viridans group streptococci, as well as a macrolide-resistant *S. pyogenes*. CEM-101 produced a greater reduction of CFU/ml and more rapid killing when compared to either TEL or the macrolides CLR and AZI Summary of Time Kill Curve Results

| Organism | Antimicrobial agent | Antimicrobial activity |
|---|---|---|
| *S. aureus* (ATCC 29213) | CEM-101 | Cidal at 2X, 4X, 8X |
| | Telithromycin | Cidal at 8X only |
| | Clarithromycin | Cidal at 8X only |
| | Azithromycin | Cidal at 8X only |
| *S. epidermidis* (095-2777A) | CEM-101 | Cidal at 2X, 4X, 8X |
| | Telithromycin | Static |
| | Clarithromycin | Static |
| | Azithromycin | Static |

-continued

| Organism | Antimicrobial agent | Antimicrobial activity |
| --- | --- | --- |
| E. faecalis (ATCC 29212) | CEM-101 | Static |
| | Telithromycin | Static |
| | Clarithromycin | Static |
| | Azithromycin | Static |
| S. pneumoniae (ATCC 49619) | CEM-101 | Cidal at 2X, 4X, 8X |
| | Telithromycin | Cidal at 2X, 4X, 8X |
| | Clarithromycin | Cidal at 2X, 4X, 8X (slow killing) |
| | Azithromycin | Cidal at 2X, 4X, 8X (slow killing) |
| S. pneumoniae (075-241B) | CEM-101 | Static |
| | Telithromycin | Static |
| S. pyogenes (117-1612A) | CEM-101 | Cidal at 8X only |
| | Telithromycin | Cidal at 8X only (slow killing) |
| | Clarithromycin | Cidal at 8X only (slow killing) |
| | Azithromycin | Cidal at 8X only (slow killing) |
| S. pyogenes (088-11708A) | CEM-101 | Cidal at 2X, 4X, 8X |
| | Telithromycin | Cidal at 2X, 4X, 8X (slow killing) |
| S. mitis (112-1885A) | CEM-101 | Cidal at 2X, 4X, 8X |
| | Telithromycin | Cidal at 2X, 4X, 8X |
| | Clarithromycin | Cidal at 8X only (slow killing) |
| | Azithromycin | Cidal at 4X and 8X (slow killing) |

CEM-101 exhibited bactericidal activity when tested against macrolide-susceptible streptococci, CoNS and macrolide-resistant CLN-susceptible S. pneumoniae. CEM-101 MBC/MIC ratios can be high for S. aureus, but some strains showed MBC results remaining within the susceptible range of concentrations.

Example

Activity on Chlamydia. CEM-101, TEL, AZI, CLR, and doxycycline were provided as powders and solubilized according to the instructions of the manufacturers. Drug suspensions were made fresh each time the assay was run.

C. pneumoniae: Isolates of C. pneumoniae tested included a reference strain (TW 183), 9 isolates from children and adults with pneumonia from the United States (AR39, T2023, T2043, W6805, CWL 029, CM-1), an isolate from a child with pneumonia from Japan (J-21), and 2 strains from bronchoalveolar lavage specimens from patients with human immunodeficiency virus infection and pneumonia from the United States (BAL15 and BAL16).

C. trachomatis: 10 isolates of C. trachomatis, including standard isolates from the ATCC (E-BOUR, F-IC-CAL3, C-HAR32, J-UW-36, L2434, D-UW-57kx, B-HAR-36) and recent clinical isolates (N18(cervical), N19(cervical), 7015 (infant eye))

In vitro susceptibility testing: Susceptibility testing of C. pneumoniae and C. trachomatis was performed in cell culture using HEp-2 cells grown in 96-well microtiter plates. Each well was inoculated with 0.1 ml of the test strain diluted to yield $10^3$ to $10^4$ IFU/per ml, centrifuged at 1,700×g for 1 hr. and incubated at 35° C. for 1 hr. Wells were aspirated and overlaid with 0.2 mL of medium containing 1 µg of cycloheximide per mL and serial two-fold dilutions of the test drug.

Duplicate plates were inoculated. After incubation at 35° C. for 48-72 hrs, cultures were fixed and stained for inclusions with fluorescein-conjugated antibody to the lipopolysaccharide genus antigen (Pathfinder, Kallestad Diagnostics, Chaska, Minn.) The minimal inhibitory concentration (MIC) is the lowest antibiotic concentration at which no inclusions were seen. The minimal bactericidal concentration (MBC) was determined by aspirating the antibiotic containing medium, washing wells twice with phosphate buffered saline and adding antibiotic-free medium. Cultures were frozen at −70° C., thawed, passed onto new cells, incubated for 72 hrs then fixed and stained as above. The MBC is the lowest antibiotic concentration that results in no inclusions after passage. All tests were run in triplicate.

Activities of CEM-101 and Other Antibiotics Against 10 Isolates of C. pneumoniae

| | MIC (µg/ml) | | | MBC (µg/ml) | |
| --- | --- | --- | --- | --- | --- |
| Drug | Range | 50% | 90% | Range | 90% |
| CEM 101 | 0.25-1.0 | 0.25 | 0.25 | 0.25-1.0 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

Activities of CEM-101 and Other Antibiotics Against 10 Isolates of C. trachomatis

| | MIC (µg/ml) | | | MBC (µg/ml) | |
| --- | --- | --- | --- | --- | --- |
| Drug | Range | 50% | 90% | Range | 90% |
| CEM 101 | 0.125-0.5 | 0.25 | 0.25 | 0.125-0.5 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

The results of this study demonstrated that CEM-101 has in vitro activity against C. trachomatis and C. pneumoniae comparable to other macrolides and ketolides.

Example

Tissue distribution. CEM-101 was well absorbed and distributed to the tissue. In the rat at 250 mg/kg/d, mean lung and liver concentrations of CEM-101 were 17 and 15-fold higher than in plasma. Lung and liver concentrations were 503 and 711-fold higher than plasma concentrations at the 200 mg/kg/d dose in monkeys. Concentrations of CEM-101 in the heart were significantly lower than levels found in lung or liver with levels 5 and 54-fold higher than plasma concentrations in rat and monkey, respectively.

What is claimed is:

1. A method for acute-exposure treatment of a host animal exposed to one or more organisms selected from the group consisting of Yersinia pestis, Francisella tularensis, and combinations thereof; the method comprising administering a composition comprising one or more compounds where the compounds are selected from the formula and pharmaceutically acceptable salts thereof, wherein:
$R^{10}$ is hydrogen or acyl;
X is H; and Y is $OR_7$; who $R_7$ is a monosaccharide or disaccharide, alkyl, aryl, heteroaryl, acyl, or C(O)$NR_8R_9$, where $R_8$ and $R_9$ are each independently selected from the group consisting of hydrogen, hydroxy, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl;
V is C(O), C(=$NR_{11}$), CH($NR_{12}$, $R_{13}$), or N($R_{14}$)$Ch_2$, where N($R_{14}$) is attached to the C-10 carbon; wherein $R_{11}$ is hydroxy or alkoxy, $R_{12}$ and $R_{13}$ are each independently selected from the group consisting of hydrogen, hydroxy, akyl, aralkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl;
W is H, F, Cl, Br, I, or OH;
A is $CH_2$, C(O), C(O)O, C(O)NH, S(O)$_2$, S(O)$_2$NH, C(O)NHS(O)$_2$;
B is $(CH_2)_n$ where n is an integer ranging from 0-10, or B is an unsaturated carbon chain of 2-10 carbons; and
C is hydrogen, hydroxy, alkyl, aralkyl, arylalkyl, alkoxy, heteroalkyl, aryl, heteroaryl, heteroarylalkyl, acyl, acyloxy, sulfonyl, ureido, or carbamoyl, each of which is optionally substituted.

2. The method of claim 1 wherein where $R_7$ is 4-nitrophenylacetyl or 2-pyridylacetyl.

3. The method of claim 1 wherein B is alkenylene.

4. The method of claim 1 wherein V is —C(O)—.

5. The method of claim 1 wherein W is H or F.

6. The method of claim 1 wherein X and Y are taken together with the attached carbon to form carbonyl.

7. The method of claim 1 wherein W is F.

8. The method of claim 1 wherein X and Y are taken together with the attached carbon to form carbonyl; and W is F.

9. The method of claim 1 wherein A is $CH_2$, B is $(CH_2)_n$, and n is an integer from 2-4.

10. The method of claim 1 wherein C is optionally substituted aryl or optionally substituted heteroaryl.

11. The method of claim 1 wherein C is 3-aminophenyl or 3-pyridinyl.

12. The method of claim 1 wherein $R^{10}$ is hydrogen.

13. A method for treating a host animal with a disease caused at least in part by one or more organisims selected from the group consisting of *Yersinia pestis, Francisella tularensis*, and combinations thereof; the method comprising administering to the host animal a composition comprising one or more compounds
where the compounds are selected from the formula and pharmaceutically acceptable salts thereof, wherein:
$R^{10}$ is hydrogen or acyl;
X is H; and Y is $OR_7$; where $R_7$ is a monosaccharide or disaccharide, alkyl, aryl, heteroaryl, acyl, or C(O)$NR_8R_9$, where $R_8$ and $R_9$ are each independently selected from the group consisting of hydrogen, hydroxyl, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl;
V is C(O), C(=$NR_{11}$), CH($NR_{12}$, $R_{13}$), or N($R_{14}$)$CH_2$, where N($R_{14}$) is attached to the C-10 carbon; wherein $R_{11}$ is hydroxy or alkoxy, $R_{12}$ and $R_{13}$ are each independently selected from the group consisting of hydrogen, hydroxy, akyl, aralkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl;
W is H, F, Cl, Br, I, or OH;
A is $CH_2$, C(O), C(O)O, C(O)NH, S(O)$_2$, S(O)$_2$NH, C(O)NHS(O)$_2$;
B is $(CH_2)_n$ where n is an integer ranging from 0-10, or B is an unsaturated carbon chain of 2-10 carbons; and
C is hydrogen, hydroxy, alkyl, aralkyl, arylalkyl, alkoxy, heteroalkyl, aryl, heteroaryl, heteroarylalkyl, acyl, acyloxy, sulfonyl, ureido, or carbamoyl, each of which is optionally substituted.

14. The method of claim 1 wherein the composition comprises a compound of the formula

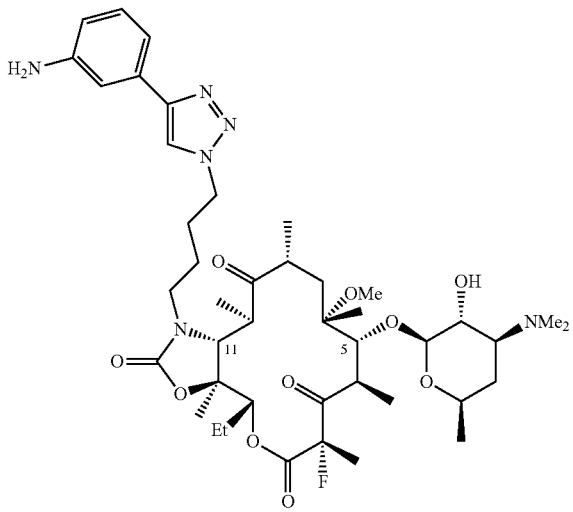 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]

or a pharmaceutically acceptable salt thereof.

15. The method of claim 1 wherein the composition comprises a compound of the formula

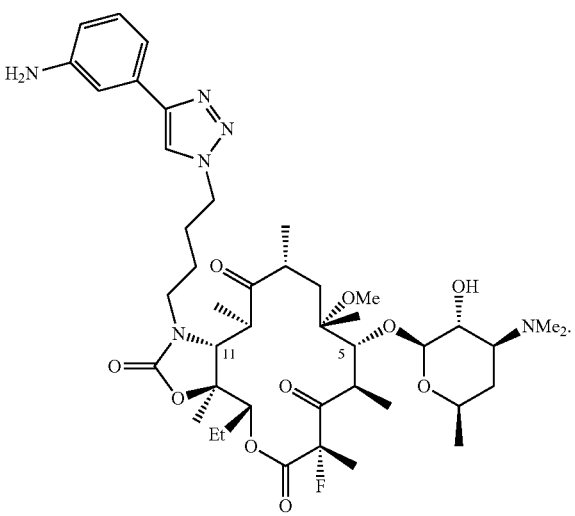 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]

16. A method for treating a disease in a host animal, where the disease is selected from the group consisting of anthax, inhalational anthrax, Legionnaire's Disease, atypical pneumonia, plague, tularemia, pneumonic tularemia, malleus, melioidosis, and combinations thereof, the method comprising administering to the host animal a composition comprising one or more compounds where the compounds are selected from the formula

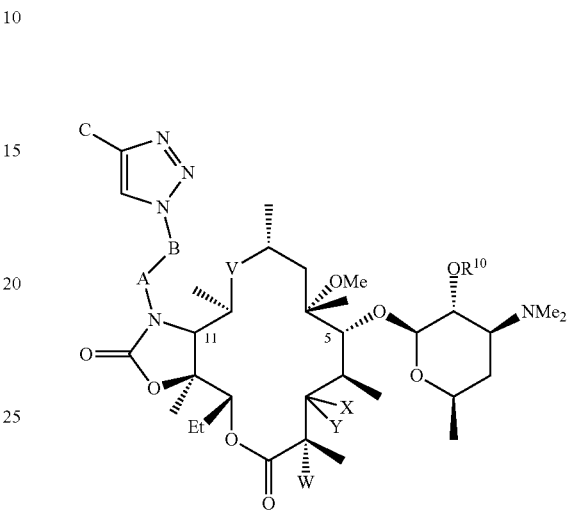

and pharmaceutically acceptable salts thereof, wherein:

$R_{10}$ is hydrogen or acyl;

X is H; and Y is $OR_7$; where $R_7$ is a monosaccharide or disaccharide, alkyl, aryl, heteroaryl, acyl, or $C(O)NR_8R_9$, where $R_8$ and $R_9$ are each independently selected from the group consisting of hydrogen, hydroxyl, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl;

V is $C(O)$, $C(=NR_{11})$, $CH(NR_{12}, R_{13})$, or $N(R_{14})CH_2$, where $N(R_{14})$ is attached to the C-10 carbon; wherein $R_{11}$ is hydroxy or alkoxy, $R_{12}$ and $R_{13}$ are each independently selected from the group consisting hydrogen, hydroxyl, akyl, aralkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxyl, alkyl, aralkyl, alkylaryl, alkoxy, heteroalkyl, aryl, heteroaryl, dimethylaminoalkyl, acyl, sulfonyl, ureido, or carbamoyl;

W is H, F, Cl, Br, I, or OH;

A is $CH_2$, $C(O)$, $C(O)O$, $C(O)NH$, $S(O)_2$, $S(O)_2NH$, $C(O)NHS(O)_2$;

B is $(CH_2)_n$ where n is an integer ranging from 0-10, or B is an unsaturated carbon chain of 2-10 carbons; and C is hydrogen, hydroxy, alkyl, aralkyl, arylalkyl, alkoxy, heteroalkyl, aryl, heteroaryl, heteroarylalkyl, acyl, acyloxy, sulfonyl, ureido, or carbamoyl, each of which is optionally substituted.

17. The method of claim 13 wherein the composition comprises a compound of the formula

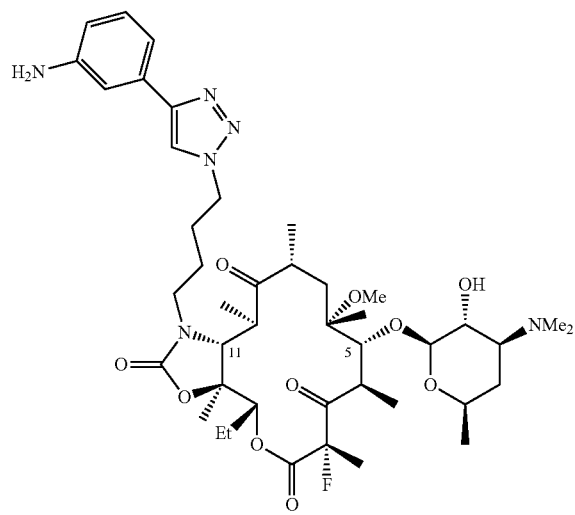 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]
or a pharmaceutically acceptable salt thereof.
18. The method of claim 13 wherein the composition comprises a compound of the formula
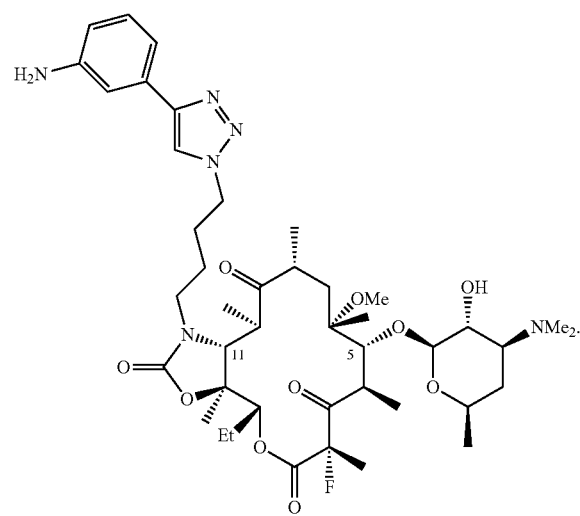 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]
19. The method of claim 16 wherein the composition comprises a compound of the formula
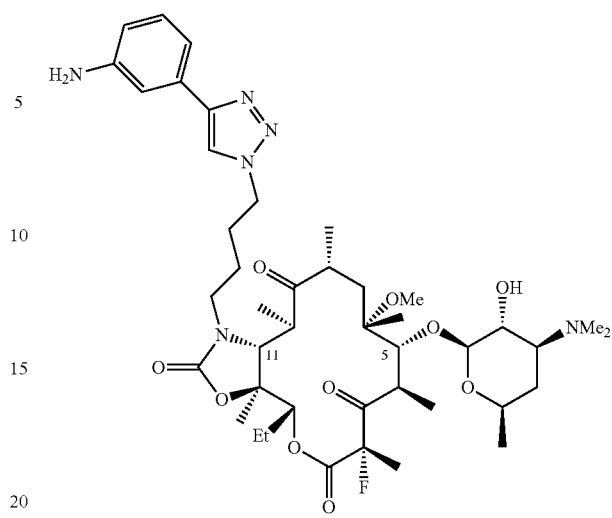
or a pharmaceutically acceptable salt thereof.
20. The method of claim 16 wherein the composition comprises a compound of the formula
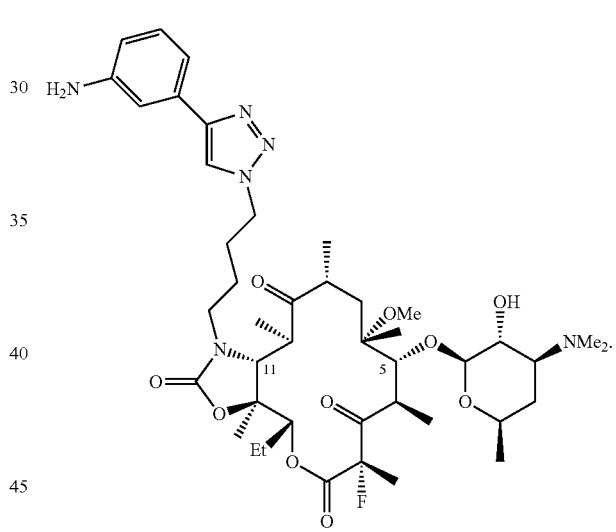
\* \* \* \* \*